(12) United States Patent
Doherty et al.

(10) Patent No.: US 6,281,194 B1
(45) Date of Patent: Aug. 28, 2001

(54) CYCLOALKYL INHIBITORS OF PROTEIN FARNESYLTRANSFERASE

(75) Inventors: Annette M. Doherty; James S. Kaltenbronn; Daniele M. Leonard; Dennis J. McNamara, all of Ann Arbor, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 09/319,422

(22) PCT Filed: Dec. 16, 1997

(86) PCT No.: PCT/US97/23280

§ 371 Date: Jun. 2, 1999

§ 102(e) Date: Jun. 2, 1999

(87) PCT Pub. No.: WO98/27109

PCT Pub. Date: Jun. 25, 1998

Related U.S. Application Data

(60) Provisional application No. 60/033,661, filed on Dec. 17, 1996, and provisional application No. 60/056,831, filed on Aug. 22, 1997.

(51) Int. Cl.[7] .................................................. C07K 5/078
(52) U.S. Cl. ............................ 514/19; 562/575; 548/344
(58) Field of Search .............................. 514/19; 548/344; 562/575

(56) References Cited

FOREIGN PATENT DOCUMENTS

| 95/12612 | 5/1995 | (WO). |
|---|---|---|
| 96 00736 | 1/1996 | (WO). |
| 98/27109 | 6/1998 | (WO). |

OTHER PUBLICATIONS

McNamara, DJ., et al. *J. of Med. Chem.,* "C–Terminal Modifictions of Histidyl–N–benzylglycinamides to give Improved Inhibition of Ras Farnesyltransferase, Cellular Activity, and Anticancer Activity in Mice", vol. 40:21; 1997, pp 3319–3322.

Leonard, D.M., et al., "Histidine–(N–benzylglycinamides): Structure–activity studies optimizing potency against ras farnesyl transferase" XP–002064323, No. 2342, vol. 38, 1997, p 350.

Sebolt–Leopold, J.S. et al., "Cellular activity of histidinyl–(N–benzylglycinamides) against Ras farnesyltransferase", XP002064324, No. 2343, vol. 38, 1997, p 350.

Przybranowski, S.A., et al., "In vivo evaluation of his-tidine–(n–benzylglycinadmides) as inhibitors of ras farnesyltransferase," XP002064325, No. 2344, vol. 38, 1997, p 350.

*Primary Examiner*—Christopher S. F. Low
*Assistant Examiner*—David Lukton
(74) *Attorney, Agent, or Firm*—Charles W. Ashbrook

(57) ABSTRACT

Novel inhibitors of protein farnesyltransferase enzymes are described, as well as methods for the preparation and pharmaceutical compositions of the same, which are useful in controlling tissue proliferative diseases, including cancer, restenosis, atherosclerosis, psoriasis and endometriosis.

20 Claims, No Drawings

CYCLOALKYL INHIBITORS OF PROTEIN FARNESYLTRANSFERASE

This application is a 371 of PCT/US97/23280 Dec. 16, 1996 which is a provisional No. 60/033,661 Dec. 17, 1996 and No. 60/056,831 Aug. 22, 1997.

The present invention relates to compounds that can be used in the medicinal field to treat, prophylactically or otherwise, uncontrolled or abnormal proliferation of tissues. Specifically, the present invention relates to compounds that inhibit the farnesyltransferase enzyme, which has been determined to activate ras proteins that in turn activate cellular division and are implicated in cancer and restenosis.

BACKGROUND OF THE INVENTION

Ras protein (or p21) has been examined extensively because mutant forms are found in 20% of most types of human cancer and greater than 50% of colon and pancreatic carcinomas (Gibbs J. B., Cell, 1991;65:1, Cartwright T., et al., Chimica. Oggi., 1992;10:26). These mutant ras proteins are deficient in the capability for feedback regulation that is present in native ras, and this deficiency is associated with their oncogenic action since the ability to stimulate normal cell division cannot be controlled by the normal endogenous regulatory cofactors. The recent discovery that the transforming activity of mutant ras is critically dependent on post-translational modifications (Gibbs J., et al., Microbiol. Rev., 1989;53:171) has unveiled an important aspect of ras function and identified novel prospects for cancer therapy.

In addition to cancer, there are other conditions of uncontrolled cellular proliferation that may be related to excessive expression and/or function of native ras proteins. Post-surgical vascular restenosis is such a condition. The use of various surgical revascularization techniques such as saphenous vein bypass grafting, endarterectomy, and transluminal coronary angioplasty are often accompanied by complications due to uncontrolled growth of neointimal tissue, known as restenosis. The biochemical causes of restenosis are poorly understood and numerous growth factors and protooncogenes have been implicated (Naftilan A. J., et al., Hypertension, 1989;13:706 and J. Clin. Invest., 83:1419; Gibbons G. H., et al., Hypertension, 1989;14:358; Satoh T., et al., Molec. Cell. Biol., 1993;13:3706). The fact that ras proteins are known to be involved in cell division processes makes them a candidate for intervention in many situations where cells are dividing uncontrollably. In direct analogy to the inhibition of mutant ras related cancer, blockade of ras dependant processes has the potential to reduce or eliminate the inappropriate tissue proliferation associated with restenosis, particularly in those instances where normal ras expression and/or function is exaggerated by growth stimulatory factors.

Ras functioning is dependent upon the modification of the proteins in order to associate with the inner face of plasma membranes. Unlike other membrane-associated proteins, ras proteins lack conventional transmembrane or hydrophobic sequences and are initially synthesized in a cytosol soluble form. Ras protein membrane association is triggered by a series of post-translational processing steps that are signaled by a carboxyl terminal amino acid consensus sequence that is recognized by protein farnesyltransferase (PFT). This consensus sequence consists of a cysteine residue located four amino acids from the carboxyl terminus, followed by two lipophilic amino acids, and the C-terminal residue. The sulfhydryl group of the cysteine residue is alkylated by farnesylpyrophosphate in a reaction that is catalyzed by protein farnesyltransferase. Following prenylation, the C-terminal three amino acids are cleaved by an endoprotease and the newly exposed alpha-carboxyl group of the prenylated cysteine is methylated by a methyl transferase. The enzymatic processing of ras proteins that begins with farnesylation enables the protein to associate with the cell membrane. Mutational analysis of oncogenic ras proteins indicate that these post-translational modifications are essential for transforming activity. Replacement of the consensus sequence cysteine residue with other amino acids gives a ras protein that is no longer farnesylated, fails to migrate to the cell membrane and lacks the ability to stimulate cell proliferation (Hancock J. F., et al., Cell, 1989;57:1617, Schafer W. R., et al., Science, 1989;245:379, Casey P. J., Proc. Natl. Acad. Sci. USA, 1989;86:8323).

Recently, protein farnesyltransferases (PFTs, also referred to as farnesyl proteintransferases (FPTs) have been identified and a specific PFT from rat brain was purified to homogeneity (Reiss Y., et al., Bioch. Soc. Trans., 1992;20:487–88). The enzyme was characterized as a heterodimer composed of one alpha-subunit (49 kDa) and one beta-subunit (46 kDa), both of which are required for catalytic activity. High level expression of mammalian PFT in a baculovirus system and purification of the recombinant enzyme in active form has also been accomplished (Chen W.-J., et al., J. Biol. Chem., 1993;268:9675).

In light of the foregoing, the discovery that the function of oncogenic ras proteins is critically dependent on their post-translational processing provides a means of cancer chemotherapy through inhibition of the processing enzymes. The identification and isolation of a protein farnesyltransferase that catalyzes the addition of a farnesyl group to ras proteins provides a promising target for such intervention. Ras farnesyl transferase inhibitors have been shown to have anticancer activity in several recent articles.

Ras inhibitor agents act by inhibiting farnesyl transferase, the enzyme that anchors the protein product of the ras gene to the cell membrane. The role of the ras mutation in transducing growth signals within cancer cells relies on the protein being in the cell membrane so with farnesyl transferase inhibited, the ras protein will stay in the cytosol and be unable to transmit growth signals: these facts are well-known in the literature.

A peptidomimetic inhibitor of farnesyl transferase B956 and its methyl ester B1086 at 100 mg/kg have been shown to inhibit tumor growth by EJ-1 human bladder carcinoma, HT1080 human fibrosarcoma and human colon carcinoma xenografts in nude mice (Nagasu, T., et al., Cancer Res., 1995;55:5310–5314). Furthermore, inhibition of tumor growth by B956 has been shown to correlate with inhibition of ras posttranslational processing in the tumor. Other ras farnesyl transferase inhibitors have been shown to specifically prevent ras processing and membrane localization and are effective in reversing the transformed phenotype of mutant ras containing cells (Sepp-Lorenzino L., et al., Cancer Rep., 1995;55:5302–5309).

In another report (Sun J., et al., Cancer Res., 1995;55:4243–4247), a ras farnesyl transferase inhibitor FTI276 has been shown to selectively block tumor growth in nude mice of a human lung carcinoma with K-ras mutation and p53 deletion. In yet another report, daily administration of a ras farnesyl transferase inhibitor L-744,832 caused tumor regression of mammary and salivary carcinomas in ras transgenic mice (Kohl et al., Nature Med., 1995;1(8) :792–748). Thus, ras farnesyl transferase inhibitors have benefit in certain forms of cancer, particularly those dependent on oncogenic ras for their growth. However, it is well-known that human cancer is often manifested when several mutations in important genes occurs, one or more of which may be responsible for controlling growth and metastases. A single mutation may not be enough to sustain growth and only after two of three mutations occur, tumors can develop and grow. It is therefore difficult to determine which of these mutations may be primarily driving the growth in a particular type of cancer. Thus, ras farnesyl transferase inhibitors can have therapeutic utility in tumors not solely dependent on oncogenic forms of ras for their growth. For example, it has been shown that various ras farnesyl transferase-inhibitors have antiproliferative effects in vivo against tumor lines with either wild-type or mutant ras (Sepp-Lorenzino, supra.). In addition, there are several ras-related proteins that are prenylated. Proteins such as R-Ras2/TC21 are ras-related proteins that are prenylated in vivo by both farnesyl transferase and geranylgeranyl transferase I (Carboni, et al., *Oncogene*, 1995;10:1905–1913). Therefore, ras farnesyl transferase inhibitors could also block the prenylation of the above proteins and therefore would then be useful in inhibiting the growth of tumors driven by other oncogenes.

With regard to the restenosis and vascular proliferative diseases, it has been shown that inhibition of cellular ras prevents smooth muscle proliferation after vascular injury in vivo (Indolfi C, et al., *Nature Med.*, 1995;1(6):541–545).

This report clearly shows that either mutant cellular P21 Ras proteins, or the inhibition of cellular P21 Ras protein function utilizing inhibitory substances, significantly reduces smooth muscle cell proliferation following arterial wall injury. This condition is generally referred to as clinical restenosis. Since it has clearly been shown that cycloalkyl inhibitors of protein farnesyl transferase are potent inhibitors of cellular P21 Ras proteins (Carboni, et al, *Oncogene*, 1995;10:1905–1913), these compounds will be effective in the treatment and prevention of smooth muscle proliferative diseases which follow vascular injury and clinical restenosis accumulation and proliferation of vascular smooth muscle.

SUMMARY OF THE INVENTION

The present invention provides compounds having the Formula I

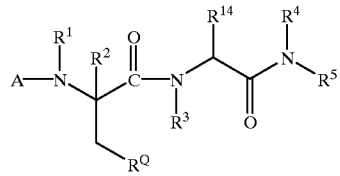

wherein $R^Q$ is

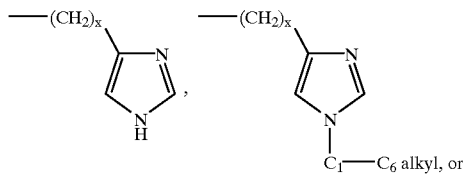

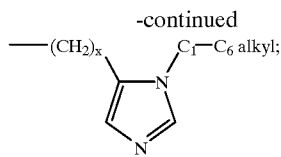

x is 0 or 1;

each $R^{14}$ is independently hydrogen or $C_1$–$C_6$ alkyl;

A is —$COR^a$, —$CO_2R^{a'}$, —$CONHR^{a'}$, —$CSR^a$,

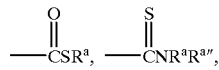

—$C(S)OR^{a'}$, —$C(S)NHR^{a'}$, —$SO_2R^a$, or —$CONR^aR^{a''}$;

$R^a$, $R^{a'}$, and $R^{a''}$ are independently $C_1$–$C_6$ alkyl, —$(CR^{14}R^{14})_m$-cycloalkyl, —$(CR^{14}R^{14})_m$-aryl, or —$(CR^{14}R^{14})_m$-heteroaryl;

each m is independently 0 to 3;

$R^1$, $R^2$, and $R^4$ are independently hydrogen or $C_1$–$C_6$ alkyl;

$R^3$ is

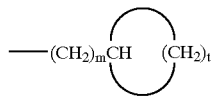

$C_1$–$C_6$ alkyl, $C_2$–$C_6$ alkenyl, —$(CR^{14}R^{14})_m$-naphthyl, —$(CH_2)_vCO_2R^{14}$, —$(CH_2)_tNR^{14}R^{14}$, —$(CH_2)_v$—O—$C_1$–$C_6$ alkyl, —$(CH_2)_t$—OH, —$(CH_2)_t$-morpholino,

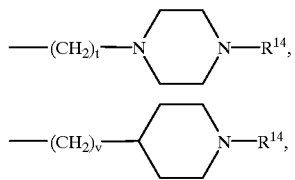

—$(CR^{14}R^{14})_m$-(phenyl substituted with $R^b$), or —$(CR^{14}R^{14})_m$-(heteroaryl substituted with $R^b$);

t is 2 to 6;

v is 1 to 6;

$R^b$ is —O-phenyl, —O-benzyl, halogen, $C_1$–$C_6$ alkyl, hydrogen, —$OC_1$–$C_6$ alkyl, —$NH_2$, —$NHR^a$, —$NR^aR^{a'}$,

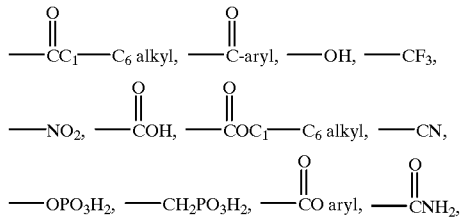

-continued

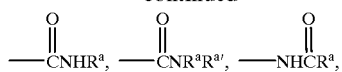

—O(CH$_2$)$_y$NR$^a$R$^{a'}$, —N$_3$, —CF$_2$CF$_3$, —SO$_2$R$^a$, —SO$_2$NR$^a$R$^{a'}$, —CHO, —OCOCH$_3$, —O(CH$_2$)$_m$-heteroaryl, —O(CH$_2$)$_m$-aryl, —O(CH$_2$)$_m$-cycloalkyl, —(CH$_2$)$_m$-aryl, —(CH$_2$)$_m$-cycloalkyl, —(CH$_2$)$_m$-heteroaryl, or —CH=CHC$_6$H$_5$;

y is 2 or 3;

R$^5$ is

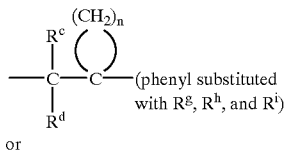

or

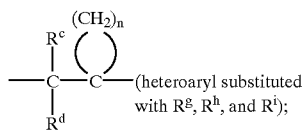

each n is independently 2, 3, or 4;

R$^i$, R$^g$, and R$^h$ are independently hydrogen, halogen, —OC$_1$–C$_6$ alkyl, C$_1$–C$_6$ alkyl, —CN, —OPO$_3$H$_2$,

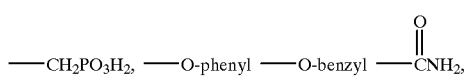

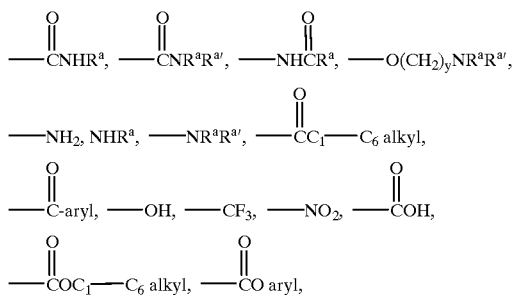

—N$_3$, —CF$_2$CF$_3$, —SO$_2$R$^a$, —SO$_2$NR$^a$R$^{a'}$, —CHO, or —OCOCH$_3$; and R$^c$ and R$^d$ are independently C$_1$–C$_6$ alkyl, —(CH$_2$)$_m$-cycloalkyl or hydrogen, and the pharmaceutically acceptable salts, esters, amides, and prodrugs thereof.

In a preferred embodiment of the compounds of Formula I

R$^1$ is hydrogen, R$^2$ is hydrogen, R$^4$ is hydrogen, R$^{14}$ is hydrogen or methyl, and A is

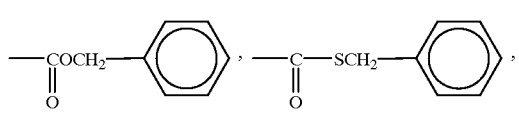

-continued

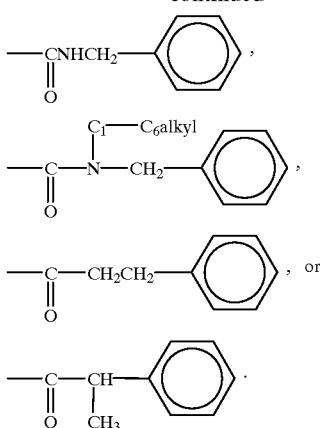

In another preferred embodiment of the compounds of Formula I

R$^3$ is

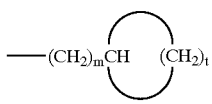

C$_1$–C$_6$ alkyl, C$_2$–C$_6$ alkenyl, —(CH$_2$)$_m$-(phenyl substituted with R$^b$) or —(CH$_2$)$_m$-(heteroaryl substituted with R$^b$).

R$^1$ is hydrogen, R$^2$ is hydrogen, R$^4$ is hydrogen, and R$^{14}$ is hydrogen or methyl.

In another preferred embodiment of the compounds of Formula I

R$^5$ is

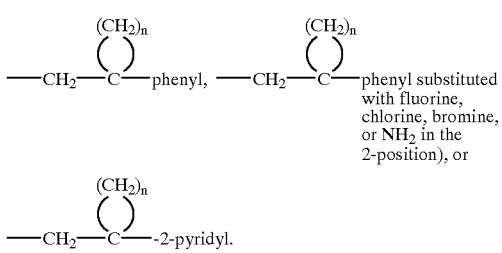

Also provided are compounds having the Formula II

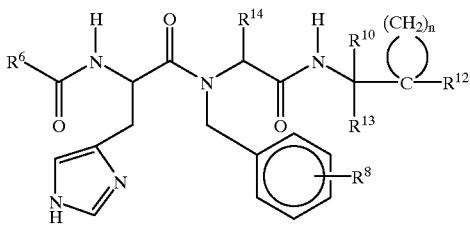

wherein $R^6$ is —O-benzyl,

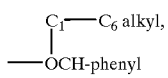

—NH-benzyl, —N($C_1$-$C_6$ alkyl)-benzyl, or —SCH$_2$-phenyl;

$R^8$ is hydrogen, halogen, $C_1$-$C_6$ alkyl, —O-benzyl, —OCH$_2$-pyridyl, —O$C_1$-$C_6$ alkyl, —CF$_3$, —OH, or -phenyl;

$R^{10}$ and $R^{13}$ are independently hydrogen or $C_1$-$C_6$ alkyl;

each n is independently 2, 3, or 4;

$R^{12}$ is

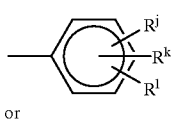

or

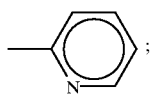

and $R^{14}$ is hydrogen or methyl;

$R^j$, $R^k$, and $R^l$ are independently hydrogen, halogen, —NH$_2$, —NHR$^a$, —O$C_1$-$C_6$ alkyl, or —$C_1$-$C_6$ alkyl, and the pharmaceutically acceptable salts, esters, amides, and prodrugs thereof.

Also provided are compounds having the Formula III

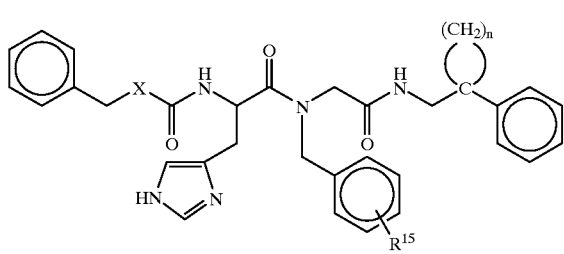

wherein each n is 2, 3, or 4;

X is NH, O, or —NCH$_3$;

$R^{15}$ is —O-benzyl, —CF$_3$, hydrogen, halogen, —OH, -phenyl, —$C_1$-$C_6$ alkyl, —OCH$_2$-pyridyl, or —O$C_{1-C_6}$ alkyl, and the pharmaceutically acceptable salts, esters, amides, and prodrugs thereof.

Also provided is a compound having Formula IV

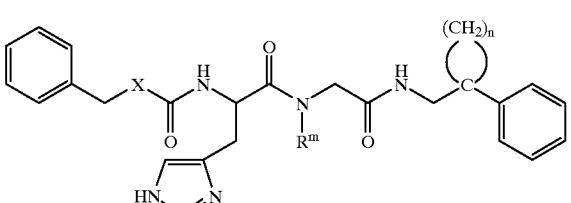

wherein

X is NH, O, or —NCH$_3$;

$R^{14}$ is hydrogen or $C_1$-$C_6$ alkyl;

$R^m$ is $C_1$-$C_6$ alkyl, $C_2$-$C_6$ alkenyl, —(CH$_2$)$_t$NR$^{14}$R$^{14}$, —(CH$_2$)$_v$—O—$C_1$-$C_6$ alkyl, —(CH$_2$)$_t$—OH, —(CH$_2$)$_t$-morpholino,

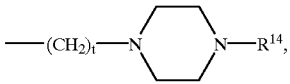

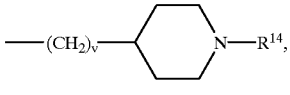

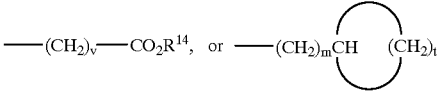

n is 2, 3, or 4;
m is 0 to 3;
t is 2 to 6; and
v is 1 to 6.

In another aspect, the present invention provides a pharmaceutically acceptable composition that comprises a compound of Formula I, II, III, or IV.

Also provided is a method of treating or preventing restenosis, the method comprising administering to a patient having restenosis or a risk of having restenosis a therapeutically effective amount of a compound of Formula I, II, III, or IV.

Also provided is a method of treating cancer, the method comprising administering to a patient having cancer a therapeutically effective amount of a compound of Formula I, II, III, or IV.

In a more preferred embodiment, the cancer is lung cancer, colon cancer, breast cancer, pancreatic cancer, thyroid cancer, or bladder cancer.

In a most preferred embodiment, the compounds of Formula I, II, III, or IV are (S)-[1-((4-Benzyloxy-benzyl)-{[(1-phenyl-cyclobutylmethyl)-carbamoyl]-methyl}-carbamoyl)-2-(1H-imidazol-4-yl)-ethyl]-carbamic acid benzyl ester;

(S)-[1-((4-Benzyloxy-benzyl)-{[(1-phenyl-cyclopropylmethyl)-carbamoyl]-methyl}-carbamoyl)-2-(1H-imidazol-4-yl)-ethyl]-carbamic acid benzyl ester;

(S)-[1-((4-Benzyloxy-benzyl)-{[(1-phenyl-cyclopentylmethyl)-carbamoyl]-methyl}-carbamoyl)-2-(1H-imidazol-4-yl)-ethyl]-carbamic acid benzyl ester;

(S)-[1-((4-Phenyl-benzyl)-{[(1-phenyl-cyclobutyl-methyl)-carbamoyl]-methyl}-carbamoyl)-2-(1H-imidazol-4-yl)-ethyl]-carbamic acid benzyl ester;

(S)-[1-((4-Methoxy-benzyl)-{[(1-phenyl-cyclobutylmethyl)-carbamoyl]-methyl}-carbamoyl)-2-(1H-imidazol-4-yl)-ethyl]-carbamic acid benzyl ester;

(S)-[1-((4-Methyl-benzyl)-{[(1-phenyl-cyclobutyl-methyl)-carbamoyl]-methyl}-carbamoyl)-2-(1H-imidazol-4-yl)-ethyl]-carbamic acid benzyl ester;

(S)-N-(4-Benzyloxy-benzyl)-2-(3-benzyl-ureido)-3-(1H-imidazol-4-yl)-N-{[(1-phenyl-cyclobutylmethyl)-carbamoyl]-methyl}-propionamide;

(S)-2-(3-Benzyl-3-methyl-ureido)-N-(4-benzyloxy-benzyl)-3-(1H-imidazol-4-yl)-N-{[(1-phenyl-cyclobutylmethyl)-carbamoyl]-methyl}-propionamide;

(S)-[1-((4-Benzyloxy-benzyl)-{[(1-phenyl-cyclobutylmethyl)-carbamoyl]-methyl}-carbamoyl)-2-(1H-imidazol-4-yl)-ethyl]-thiocarbamic acid S-benzyl ester;

(S)-(2-(1H-Imidazol-4-yl)-1-{{[(1-phenyl-cyclobutylmethyl)-carbamoyl]-methyl}-[4-(pyridin-2-yl-methoxy)-benzyl]-carbamoyl}-ethyl)-carbamic acid benzyl ester;

(S)-(1-((Cyclohexyl-methyl)-{[(1-phenyl-cyclobutylmethyl)-carbamoyl]-methyl}-carbamoyl)-2-(1H-imidazol-4-yl)-ethyl]-carbamic acid benzyl ester;

(S)-(1-((Isobutyl)-{[(1-phenyl-cyclobutylmethyl)-carbamoyl]-methyl}-carbamoyl)-2-(1H-imidazol-4-yl)-ethyl]-carbamic acid benzyl ester;

(S)-2-(3-Benzyl-3-methyl-ureido)-3-(1H-imidazol-4-yl)-N-(4 methyl-benzyl)-N-{[(1-phenyl-cyclobutylmethyl)-carbamoyl]-methyl}-propionamide;

(S)-[1-[(4-Benzyloxy-benzyl)-({[1-(2,6-dichloro-phenyl)-cyclobutylmethyl]-carbamoyl}-methyl)-carbamoyl]-2-(1H-imidazol-4-yl)-ethyl]-carbamic acid benzyl ester;

[(S)-trans]-[1-(But-2-enyl-{[(1-phenyl-cyclobutyl-methyl)-carbamoyl]-methyl}-carbamoyl)-2-(3H-imidazol-4-yl)-ethyl]-carbamic acid benzyl ester;

(S)-[2-(3H-Imidazol-4-yl)-1-({[(1-phenyl-cyclobutylmethyl)-carbamoyl]-methyl}-propyl-carbamoyl)-ethyl]-carbamic acid benzyl ester;

Benzyl N-((1S)-1-(1H-4-imidazolylmethyl)-2-oxo-2-(2-oxo-2-[(1-phenylcyclobutyl)methyl]aminoethyl)[(1R)-1-phenylethyl]aminoethyl)carbamate;

(S)-[1-((1,1-Dimethyl-2-phenyl-ethyl)-{[(1-phenyl-cyclobutylmethyl)-carbamoyl]-methyl}-carbamoyl)-2-(3H-imidazol-4-yl)-ethyl]-carbamic acid benzyl ester;

Benzyl N-((1S)-1-(1H-4-imidazolylmethyl)-2-oxo-2-(2-oxo-2-[(1-phenylcyclobutyl)methyl]aminoethyl)[(1S)-1-phenylethyl]aminoethyl)carbamate;

Benzyl N-[(1S)-2-[(2-hydroxyethyl)(2-oxo-2-[(1-phenylcyclobutyl)methyl]aminoethyl)amino]-1-(1H-4-imidazolylmethyl)-2-oxoethyl]carbamate;

3-[[(2S)-2-[(Benzyloxy)carbonyl]amino-3-(1H-4-imidazolyl)propanoyl](2-oxo-2-[(1-phenylcyclobutyl)-methyl]aminoethyl)amino]propanoic acid;

Methyl 3-[[(2S)-2-[(benzyloxy)carbonyl]amino-3-(1H-4-imidazolyl)propanoyl](2-oxo-2-[(1-phenylcyclobutyl)methyl]aminoethyl)amino]propanoate;

Benzyl N-[(1S)-2-[(2-aminoethyl)(2-oxo-2-[(1-phenylcyclobutyl)methyl]aminoethyl)amino]-1-(1H-4-imidazolylmethyl)-2-oxoethyl]carbamate;

Benzyl N-(1S)-1-(1H-4-imidazolylmethyl)-2-[[2-(methylamino)ethyl](2-oxo-2-[(1-phenylcyclobutyl)-methyl]aminoethyl)amino]-2-oxoethylcarbamate;

Benzyl N-(1S)-1-(1H-4-imidazolylmethyl)-2-[(2-(methoxyethyl)(2-oxo-2-[(1-phenylcyclobutyl) methyl]-aminoethyl)amino]-2-oxoethylcarbamate;

Benzyl N-(1S)-1-(1H-4-imidazolylmethyl)-2-[(2-(morpholinoethyl)(2-oxo-2-[(1-phenylcyclobutyl) methyl]-aminoethyl)amino]-2-oxoethylcarbamate;

Benzyl N-(1S)-1-(1H-4-imidazolylmethyl)-2-[(2-(methyl-2-phenylpropyl)(2-oxo-2-[(1-phenylcy-clobutyl)-methyl]aminoethyl)amino]-2-oxoethylcarbamate; and 1-Phenylethyl N-[(1S)-2-[[4-(benzyloxy)-1,5-cyclohexadienyl]methyl(2-oxo-2-[(1-phenylcy-clobutyl)-methyl]aminoethyl)amino]-1-(1H-4-imidazolylmethyl)-2-oxoethyl]carbamate.

DETAILED DESCRIPTION OF THE INVENTION

The present invention provides a compound having the Formula I

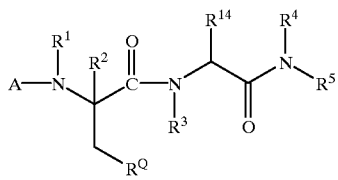

wherein
$R^Q$ is

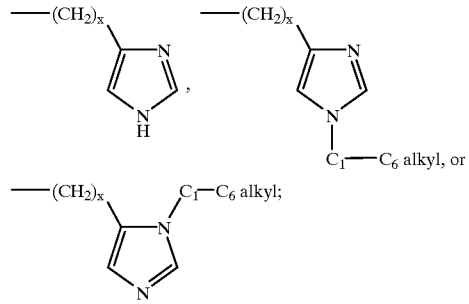

x is 0 or 1;
each $R^{14}$ is independently hydrogen or $C_1$–$C_6$ alkyl;
A is —$COR^a$, —$CO_2R^a$, —$CONHR^{a'}$, —$CSR^a$,

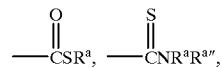

—$C(S)OR^{a'}$, —$C(S)NHR^{a'}$, —$SO_2R^a$, or —$CONR^aR^{a''}$;
$R^a$, $R^{a'}$, and $R^{a''}$ are independently $C_1$–$C_6$ alkyl, —$(CR^{14}R^{14})_m$-cycloalkyl, —$(CR^{14}R^{14})_m$-aryl, or —$(CR^{14}R^{14})_m$-heteroaryl;
each m is independently 0 to 3;
$R^1$, $R^2$, and $R^4$ are independently hydrogen or $C_1$–$C_6$ alkyl;
$R^3$ is

$C_1$–$C_6$ alkyl, $C_2$–$C_6$ alkenyl, —$(CR^{14}R^{14})_m$-naphthyl, —$(CH_2)_vCO_2R^{14}$, —$(CH_2)_tNR^{14}R^{14}$, —$(CH_2)_v$—O—$C_1$–$C_6$ alkyl, —$(CH_2)_t$—OH, —$(CH_2)_t$-morpholino,

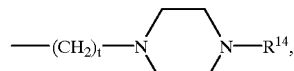

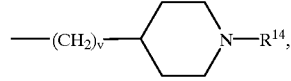

—$(CR^{14}R^{14})_m$-(phenyl substituted with $R^b$), or
—$(CR^{14}R^{14})_m$-(heteroaryl substituted with $R^b$);
t is 2 to 6;

v is 1 to 6;

$R^b$ is —O-phenyl, —O-benzyl, halogen, $C_1$–$C_6$ alkyl, hydrogen, —$OC_1$–$C_6$ alkyl, —$NH_2$, —$NHR^a$, —$NR^aR^{a\prime}$, —$\overset{O}{\underset{\parallel}{C}}C_1$—$C_6$ alkyl, —$\overset{O}{\underset{\parallel}{C}}$-aryl, —$\overset{O}{\underset{\parallel}{C}}NH_2$, —$\overset{O}{\underset{\parallel}{C}}NHR^a$, —$\overset{O}{\underset{\parallel}{C}}NR^aR^{a\prime}$, —$NH\overset{O}{\underset{\parallel}{C}}R^a$, —$O(CH_2)_yNR^aR^{a\prime}$, —OH, —$CF_3$, —$NO_2$, —$\overset{O}{\underset{\parallel}{C}}OH$, —$\overset{O}{\underset{\parallel}{C}}OC_1$—$C_6$ alkyl, —CN, —$OPO_3H_2$, —$CH_2PO_3H_2$, —$\overset{O}{\underset{\parallel}{C}}O$ aryl, —$N_3$, —$CF_2CF_3$, —$SO_2R^a$, —$SO_2NR^aR^{a\prime}$, —CHO, —$O(CH_2)_m$-aryl, —$O(CH_2)_m$-cycloalkyl, —$(CH_2)_m$-aryl, —$(CH_2)_m$-cycloalkyl, —$(CH_2)_m$-heteroaryl, —CH=$CHC_6H_5$, —$OCOCH_3$, or —$O(CH_2)_m$-heteroaryl;

y is 2 or 3;

$R^5$ is

—$\underset{R^d}{\overset{R^c}{\underset{|}{\overset{|}{C}}}}$—$\overset{(CH_2)_n}{\overset{\frown}{C}}$—(phenyl substituted with $R^g$, $R^h$, and $R^i$)

or

—$\underset{R^d}{\overset{R^c}{\underset{|}{\overset{|}{C}}}}$—$\overset{(CH_2)_n}{\overset{\frown}{C}}$—(heteroaryl substituted with $R^g$, $R^h$, and $R^i$);

each n is independently 2, 3, or 4;

$R^i$, $R^g$, and $R^h$ are independently hydrogen, halogen, —$OC_1$–$C_6$ alkyl, $C_1$–$C_6$ alkyl, —CN, —$OPO_3H_2$, —$CH_2PO_3H_2$, —O-phenyl, —O-benzyl, —$\overset{O}{\underset{\parallel}{C}}NH_2$, —$\overset{O}{\underset{\parallel}{C}}NHR^a$, —$\overset{O}{\underset{\parallel}{C}}NR^aR^{a\prime}$, —$NH\overset{O}{\underset{\parallel}{C}}R^a$, —$O(CH_2)_yNR^aR^{a\prime}$, —$NH_2$, $NHR^a$, —$NR^aR^{a\prime}$, —$\overset{O}{\underset{\parallel}{C}}C_1$—$C_6$ alkyl, —$\overset{O}{\underset{\parallel}{C}}$-aryl, —OH, —$CF_3$, —$NO_2$, —$\overset{O}{\underset{\parallel}{C}}OH$, —$\overset{O}{\underset{\parallel}{C}}OC_1$—$C_6$ alkyl, —$\overset{O}{\underset{\parallel}{C}}O$ aryl, —$N_3$, —$CF_2CF_3$, —$SO_2R^a$, —$SO_2NR^aR^{a\prime}$, —CHO, or —$OCOCH_3$; and $R^c$ and $R^d$ are independently $C_1$–$C_6$ alkyl, —$(CH_2)_m$-cycloalkyl or hydrogen, and the pharmaceutically acceptable salts, esters, amides, and prodrugs thereof.

Also provided are compounds having the Formula II

II wherein $R^6$ is —O-benzyl,

—$\underset{OCH\text{-phenyl}}{\overset{C_1-C_6 \text{ alkyl}}{|}}$

—NH-benzyl, —N($C_1$–$C_6$ alkyl)-benzyl, or —$SCH_2$-phenyl;

$R^8$ is hydrogen, halogen, $C_1$–$C_6$ alkyl, —O-benzyl, —$OCH_2$-pyridyl, —$OC_1$–$C_6$ alkyl, —$CF_3$, —OH, or -phenyl;

$R^{12}$ is and and $R^{10}$ and $R^{13}$ are independently hydrogen or $C_1$–$C_6$ alkyl;

n is 2, 3, or 4;

$R^{14}$ is hydrogen or methyl; and $R^j$, $R^k$, and $R^l$ are independently hydrogen, halogen, —$NH_2$, —$NHR^a$, —$OC_1$–$C_6$ alkyl or —$C_1$–$C_6$ alkyl, and the pharmaceutically acceptable salts, esters, amides, and prodrugs thereof.

Also provided are compounds having the Formula III

III wherein each n is 2, 3, or 4;

X is NH, O, or —$NCH_3$;

$R^{15}$ is —O-benzyl, —$CF_3$, hydrogen, halogen, —OH, -phenyl, —$C_1$–$C_6$ alkyl, —$OCH_2$-pyridyl, or —OC$_1$–C$_6$ alkyl, and the pharmaceutically acceptable salts, esters, amides, and prodrugs thereof.

Also provided is a compound having Formula IV

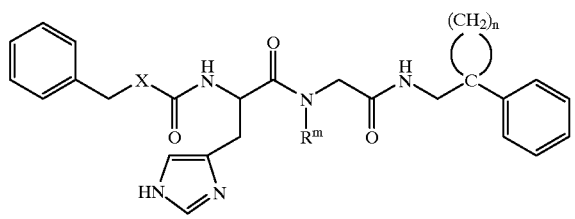

IV wherein

X is NH, O, or —NCH$_3$;

R$^m$ is C$_1$–C$_6$ alkyl, C$_2$–C$_6$ alkenyl, —(CH$_2$)$_t$NR$^{14}$R$^{14}$, —(CH$_2$)$_v$—O—C$_1$–C$_6$ alkyl, —(CH$_2$)$_t$—OH, —(CH$_2$)$_t$-morpholino,

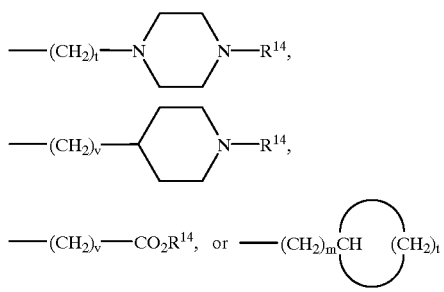

each R$^{14}$ is independently hydrogen or C$_1$–C$_6$ alkyl;

n is 2, 3, or 4;

m is 0 to 3;

t is 2 to 6; and v is 1 to 6.

The term "alkyl" means a straight or branched hydrocarbon having from 1 to 6 carbon atoms and includes, for example, methyl, ethyl, n-propyl, isopropyl, n-butyl, sec-butyl, isobutyl, tert-butyl, n-pentyl, n-hexyl, and the like.

The term "cycloalkyl" means a saturated hydrocarbon ring which contains from 3 to 7 carbon atoms, for example, cyclopropyl, cyclobutyl, cyclopentyl, cyclohexyl, adamantyl, and the like.

The term "aryl" means an aromatic ring which is a phenyl, 5-fluorenyl, 1-naphthyl, or 2-naphthyl group, unsubstituted or substituted by 1 to 3 substituents selected from alkyl, O-alkyl and S-alkyl, OH, SH, F, Cl, Br, I, CF$_3$, NO$_2$, NH$_2$, NHCH$_3$, N(CH$_3$)$_2$, NHCO-alkyl, —OCH$_2$C$_6$H$_5$, (CH$_2$)$_m$CO$_2$H, (CH$_2$)$_m$CO$_2$-alkyl, (CH$_2$)$_m$SO$_3$H, (CH$_2$)$_m$PO$_3$H$_2$, (CH$_2$)$_m$PO$_3$(alkyl)$_2$, (CH$_2$)$_m$SO$_2$NH$_2$, and (CH$_2$)$_m$SO$_2$NH-alkyl wherein alkyl is defined as above and m=0, 1, 2, or 3.

The term "heteroaryl" means a heteroaromatic ring which is a 2- or 3-thienyl, 2- or 3-furanyl, 2- or 3-pyrrolyl, 2-, 3-, or 4-pyridyl, imidazolyl, 2-, 3-, 4-, 5-, 6-, or 7-indolyl group, unsubstituted or substituted by 1 or 2 substituents from the group of substituents described above for aryl.

The symbol "—" means a bond.

The term "patient" means all animals including humans. Examples of patients include humans, cows, dogs, cats, goats, sheep, and pigs.

A "therapeutically effective amount" is an amount of a compound of the present invention that when administered to a patient ameliorates a symptom of restenosis or cancer or prevents restenosis. A therapeutically effective amount of a compound of the present invention can be easily determined by one skilled in the art by administering a quantity of a compound to a patient and observing the result. In addition, those skilled in the art are familiar with identifying patients having cancer or restenosis or who are at risk of having restenosis.

The term "cancer" includes, but is not limited to, the following cancers:

breast;

ovary;

cervix;

prostate;

testis;

esophagus;

glioblastoma;

neuroblastoma;

stomach;

skin, keratoacanthoma;

lung, epidermoid carcinoma, large cell carcinoma, adenocarcinoma;

bone;

colon, adenocarcinoma, adenoma;

pancreas, adenocarcinoma;

thyroid, follicular carcinoma, undifferentiated carcinoma, papillary carcinoma;

seminoma;

melanoma;

sarcoma;

bladder carcinoma;

liver carcinoma and biliary passages;

kidney carcinoma;

myeloid disorders;

lymphoid disorders, Hodgkins, hairy cells;

buccal cavity and pharynx (oral), lip, tongue, mouth, pharynx;

small intestine;

colon-rectum, large intestine, rectum;

brain and central nervous system; and leukemia.

The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgement, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphtholate mesylate, glucoheptonate, lactobionate and laurylsulphonate salts, and the like. These may include cations based on the alkali and alkaline earth metals, such as sodium, lithium, potassium, calcium, magnesium and the like, as well as nontoxic ammonium, quaternary ammonium, and amine cations including, but not limited to ammonium, tetramethylammonium, tetraethylammonium, methylamine, dimethylamine, trimethylamine, triethylamine, ethylamine, and the like. (See, for example, S. M. Berge, et al., "Pharmaceutical Salts," *J. Pharm. Sci.*, 1977;66:1–19 which is incorporated herein by reference.)

Examples of pharmaceutically acceptable, non-toxic esters of the compounds of this invention include $C_1$–$C_6$ alkyl esters wherein the alkyl group is a straight or branched chain. Acceptable esters also include $C_5$–$C_7$ cycloalkyl esters as well as arylalkyl esters such as, but not limited to benzyl. $C_1$–$C_4$ alkyl esters are preferred. Esters of the compounds of the present invention may be prepared according to conventional methods.

Examples of pharmaceutically acceptable, non-toxic amides of the compounds of this invention include amides derived from ammonia, primary $C_1$–$C_6$ alkyl amines and secondary $C_1$–$C_6$ dialkyl amines wherein the alkyl groups are straight or branched chain. In the case of secondary amines the amine may also be in the form of a 5- or 6-membered heterocycle containing one nitrogen atom. Amides derived from ammonia, $C_1$–$C_3$ alkyl primary amines and $C_1$–$C_2$ dialkyl secondary amines are preferred. Amides of the compounds of the invention may be prepared according to conventional methods.

The term "prodrug" refers to compounds that are rapidly transformed in vivo to yield the parent compound of the above formulae, for example, by hydrolysis in blood. A thorough discussion is provided in T. Higuchi and V. Stella, "Pro-drugs as Novel Delivery Systems," Vol 14 of the A.C.S. Symposium Series, and in *Bioreversible Carriers in Drug Design*, ed. Edward B. Roche, American Pharmaceutical Association and Pergamon Press, 1987, both of which are hereby incorporated by reference.

The compounds of the present invention can be administered to a patient alone or as part of a composition that contains other components such as excipients, diluents, and carriers, all of which are well-known in the art. The compositions can be administered to humans and animals either orally, rectally, parenterally (intravenously, intramuscularly or subcutaneously), intracisternally, intravaginally, intraperitoneally, intravesically, locally (powders, ointments or drops), or as a buccal or nasal spray.

Compositions suitable for parenteral injection may comprise physiologically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil), and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid; (b) binders, as for example, carboxymethylcellulose, alignates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate, (e) solution retarders, as for example paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well-known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, Cremophor EL (a derivative of castor oil and ethylene oxide; purchased from Sigma Chemical Co., St. Louis, Mo.), polyethyleneglycols and fatty acid esters of sorbitan or mixtures of these substances, and the like.

Besides such inert diluents, the composition can also include adjuvants, such as wetting agents, emulsifying and suspending agents, sweetening, flavoring and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar—agar and tragacanth, or mixtures of these substances, and the like.

Compositions for rectal administrations are preferably suppositories which can be prepared by mixing the compounds of the present invention with suitable non-irritating excipients or carriers such as cocoa butter, polyethyleneglycol, or a suppository wax, which are solid at ordinary temperatures but liquid at body temperature and therefore, melt in the rectum or vaginal cavity and release the active component.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

The compounds of the present invention can be administered to a patient at dosage levels in the range of about 0.1 to about 2,000 mg per day. For a normal human adult having a body weight of about 70 kilograms, a dosage in the range of about 0.01 to about 100 mg per kilogram of body weight per day is preferable. The specific dosage used, however, can vary. For example, the dosage can depended on a numbers of factors including the requirements of the patient, the severity of the condition being treated, and the pharmacological activity of the compound being used. The determination of optimum dosages for a particular patient is well known to those skilled in the art.

The compounds of the present invention can exist in different stereoisomeric forms by virtue of the presence of asymmetric centers in the compounds. It is contemplated that all stereoisomeric forms of the compounds as well as mixtures thereof, including racemic mixtures, form part of this invention.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The examples presented below are intended to illustrate particular embodiments of the invention, and are not intended to limit the scope of the specification or the claims in any way.

Scheme 1 shows a general method by which the compounds of the present invention can be prepared.

SCHEME 1
Preparation of Example 1

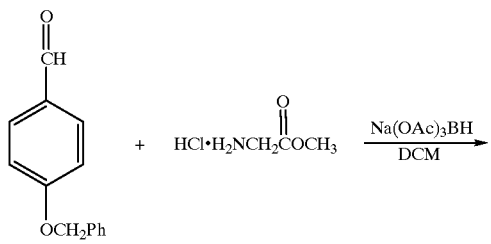

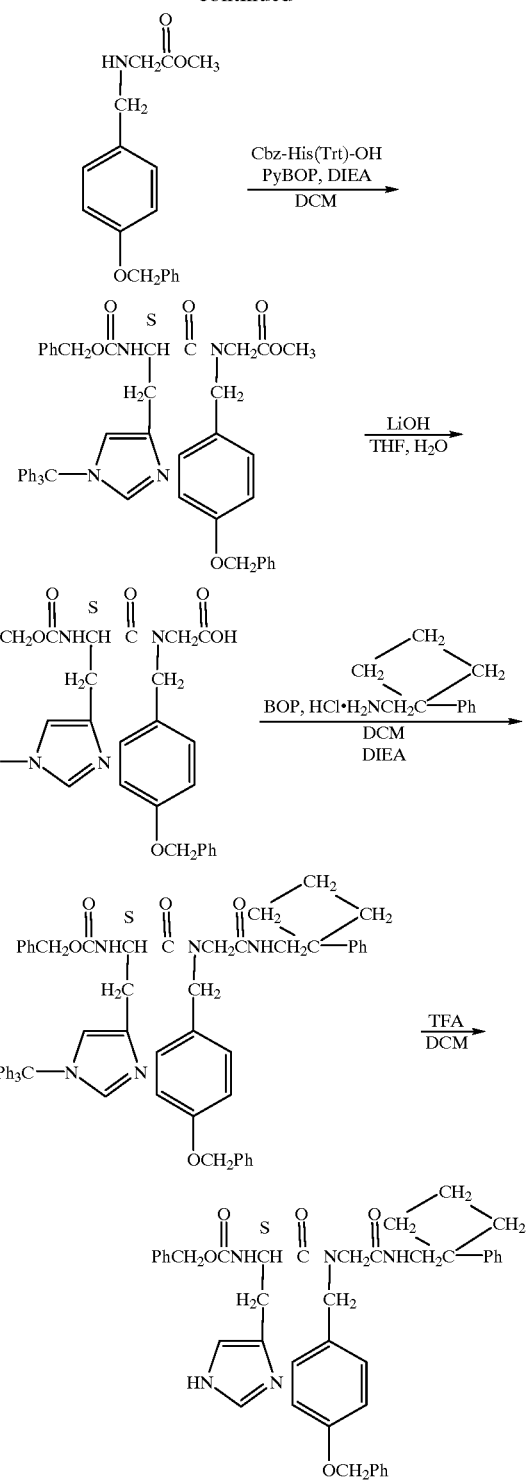

SCHEME 2
Preparation of Example 10

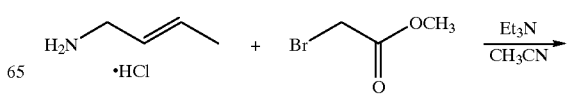

19

-continued

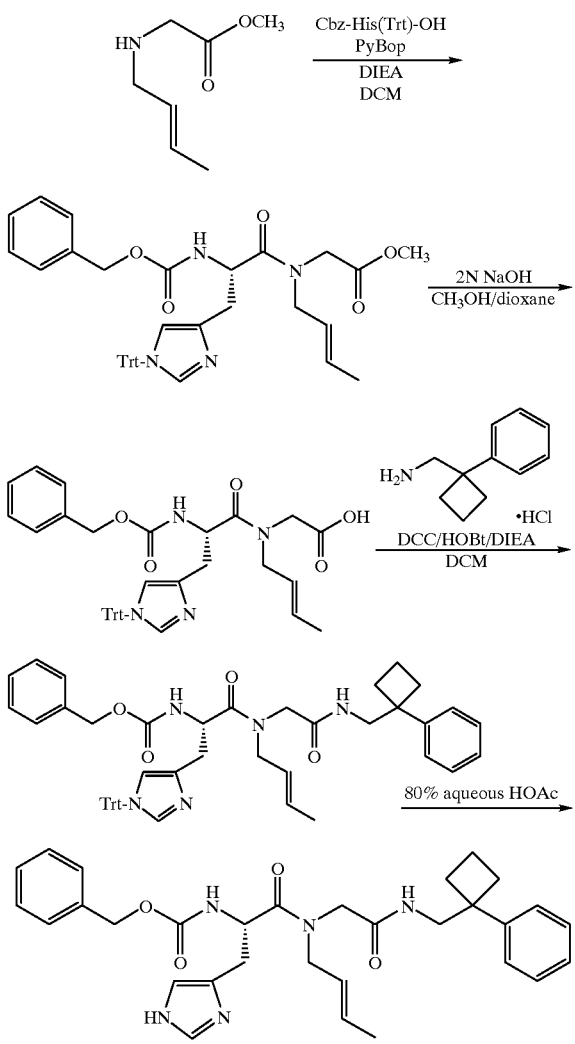

In Step 4 of Scheme 1, the alternate condensing agents PyBOP; dicyclohexylcarbodiimide (DCC)/1-hydroxybenzotriazole (HOBt); O-benzotriazol-1-yl-N,N,N',N'-tetramethyluronium hexafluorophosphate (HBTU); and O-(7-azabenzotriazol-1yl)-N,N,N',N'-tetramethyluronium hexafluorophosphate (HATU)/1-hydroxy-7-azabenzotriazole (HOAt) can also be used. In Step 5, 80% acetic acid/water at 90° C. for 30 minutes can also be used.

Abbreviations

| | |
|---|---|
| DCM | Dichloromethane |
| Na(OAc)$_3$BH | Sodium triacetoxyborohydride |
| PyBOP | Benzotriazole-1-yl-oxy-tris-pyrrolidino-phosphonium hexafluorophosphate |
| DIEA | Diisopropylethylamine |
| THF | Tetrahydrofuran |
| BOP | Benzotriazole-1-yl-oxy-tris-(dimethylamino)-phosphonium hexafluorophosphate |
| TFA | Trifluoroacetic acid |
| EA | Ethyl acetate |

20

EXAMPLE 1

(S)-[1-((4-Benzyloxy-benzyl)-{[1-(phenyl-cyclobutylmethyl)-carbamoyl]-methyl}-carbamoyl)-2-(1H-imidazol-4-yl)-ethyl]-carbamic Acid benzyl ester Step 1: [(4-Benzyloxy-benzyl)-amino]-acetic Acid methyl ester To a suspension of glycine methyl ester hydrochloride (1.26 g, 10 mmol) and 4-benzyloxybenzaldehyde (2.12 g, 10 mmol) in DCM (50 mL), under nitrogen at 0° C., was added Na(OAc)$_3$BH (3.81 g, 15 mmol). The suspension was allowed to warm to room temperature and stirred for 4 hours. The suspension was poured into saturated aqueous NaHCO$_3$, and the layers were separated. The aqueous layer was extracted with DCM (4×25 mL). The combined organic extracts were dried over MgSO$_4$ and concentrated. Flash chromatography (EA) gave 1.15 g (40.4%) of the title compound as a white solid; mp 57–58° C.

Analysis calculated for $C_{17}H_{19}NO_3$: C, 71.56; H, 6.71; N, 4.91. Found: C, 71.45; H, 6.99; N, 4.92.

Mass spectrum (MS)—Chemical Ionization (CI): Calculated for M+1: 286; Found: 286.

The NMR spectrum was consistent with the structure.

Step 2: (S)-{(4-Benzyloxy-benzyl)-[2-benzyloxy-carbonylamino-3-(1-trityl-1H-imidazoyl-4-yl)-propionyl]-amino}-acetic Acid methyl Ester To a solution of (S)-2-benzyloxycarbonylamino-3-(1-trityl-1H-imidazol-4-yl)-propionic acid [Cbz-His(Trt)] (Hudspeth J. P., Kaltenbronn J. S., Repine J. T., Roark W. H., Stier M. A., *Renin Inhibtors III*. U.S. Pat. No. 4,735,933; 1988) (5.85 g, 11 mmol) and PyBOP (5.72 g, 11 mmol) in DCM (100 mL) at 0° C. was added the methyl ester from Step 1 above (2.85 g, 10 mmol), followed by DIEA (3.05 mL, 17.5 mmol). The solution was warmed to room temperature and stirred under nitrogen for 5 hours. The solution was poured into saturated aqueous NaHCO$_3$, and the layers were separated. The aqueous layer was extracted with DCM (4×50 mL). The combined organic layers were dried over MgSO$_4$ and concentrated. Flash chromatography (10% methanol [MeOH] in DCM) gave 4.48 g (55.4%) of the title compound as a white foam.

Analysis calculated for $C_{50}H_{46}N_4O_6 \cdot 0.5 \, H_2O$: C, 74.33; H, 5.86; N, 6.93. Found: C, 74.00; H, 5.75; N, 6.79.

MS-electrospray (ES): Calculated for M+1: 799.3; Found: 799.3.

The NMR spectrum was consistent with the structure.

Step 3: (S)-{(4 -Benzyloxy-benzyl)-[2-benzyloxy-carbonylamino-3-(1-trityl-1H-imidazol-4-yl)-propionyl]-amino}-acetic Acid To a solution of the methyl ester from Step 2 above (0.799 g, 1 mmol) in THF (10 mL) was added H$_2$O (3.3 mL) to give a solution. The solution was cooled to 0° C. and treated with LiOH.H$_2$O (0.050 g, 1.2 mmol). The solution was warmed to room temperature and stirred for 4 hours. Another batch of LiOH.H$_2$O (0.050 g, 1.2 mmol) was added, and the suspension was stirred for another 1.5 hours. The suspension was concentrated, diluted with H$_2$O, and adjusted to pH=2 (paper) with 1 M HCl. The suspension was extracted with EA (4×20 mL). The organic extracts were dried over MgSO$_4$ and concentrated. Flash chromatography (10% MeOH in DCM) gave 0.706 g (89.0%) of the title compound as a white foam.

Analysis calculated for $C_{49}H_{44}N_4O_6 \cdot 0.5 \, H_2O$: C, 74.13; H, 5.71; N, 7.05. Found: C, 74.22; H, 5.70; N, 6.81.

MS-ES: Calculated for M+1: 785.3; Found: 785.2.

The NMR and IR spectra were consistent with the structure.

4: (S)-[1-((4-Benzyloxy-benzyl)-{[(1-phenyl-cyclobutylmethyl)-carbamoyl]-methyl}-carbamoyl)-2-(1-trityl-1H-imidazol-4-yl)-ethyl]-carbamic Acid benzyl Ester To a suspension of the acid from Step 3 above (0.500 g, 0.637 mmol), BOP (0.310 g, 0.70 mmol) and C-(1-phenyl-cyclobutyl)-methylamine hydrochloride (Bridges A. J., Hamilton H. W., Moos W. H., Szotek D. L., "N[6]-Substituted Adenosines". U.S. Pat. No. 4,755,594; 1988) (0.139 g, 0.701 mmol) in DCM (10 mL) at 0° C. was added DIEA (0.29 mL, 1.75 mmol). The resulting solution was stirred at room temperature overnight. The solution was poured into saturated aqueous $NaHCO_3$, and the layers were separated. The aqueous layer was extracted with DCM (3×50 mL). The combined organic layers were washed with $H_2O$, then twice with 0.5 M HCl, then once with saturated aqueous $NaHCO_3$, dried over $MgSO_4$, and concentrated. Flash chromatography (10% MeOH in DCM) gave 0.49 g of the title compound as a white foam which was not characterized and was used directly in the next reaction.

Step 5: (S)-[1-((4-Benzyloxy-benzyl)-{[(1-phenyl-cyclobutylmethyl)-carbamoyl]-methyl}-carbamoyl)-2-(1-H-imidazol-4-yl)-ethyl]-carbamic Acid benzyl Ester To a solution of the trityl compound from Step 4 above (0.49 g) in DCM (10 mL) was added TFA (10 mL). The solution was stirred at room temperature for 2 hours and then concentrated. The residue was dissolved in DCM and washed with saturated aqueous $NaHCO_3$. The aqueous layer was extracted with DCM (2×50 mL). The combined organic extracts were dried over $MgSO_4$ and concentrated. Flash chromatography (10% MeOH in DCM) gave 0.22 g (50% yield over two steps) of the title compound as a white foam.

Analysis calculated for $C_{41}H_{43}N_5O_5 \cdot 0.5\ H_2O$: C, 70.87; H, 6.38; N, 10.08. Found: C, 70.81; H, 6.46; N, 9.91.
MS—Atmospheric Pressure Chemical Ionization (APCI): Calculated for M+1: 686.3; Found: 686.3.
The NMR and IR spectra were consistent with the structure.

EXAMPLE 2

(S)-[1-((4-Benzyloxy-benzyl)-{[(1-phenyl-cyclopropylmethyl)-carbamoyl]-methyl}-carbamoyl)-2-(1H-imidazol-4-yl)-ethyl-carbamic Acid benzyl Ester According to Example 1, Steps 4 and 5, by substituting C-(1-phenyl-cyclopropyl)-methylamine hydrochloride (U.S. Pat. No. 4,755,594; 1988) for C-(1-phenyl-cyclobutyl)-methylamine hydrochloride, 0.11 g (26% yield over two steps) of the title compound was obtained as a white foam.

Analysis calculated for $C_{40}H_{41}N_5O_5 \cdot 0.5\ H_2O$: C, 70.57; H, 6.22; N, 10.29. Found: C, 70.43; H, 5.98; N, 10.25.
MS-APCI: Calculated for M+1: 672.3; Found: 672.3.
The NMR and IR spectra were consistent with the structure.

EXAMPLE 3

(S)-(2-(1H-Imidazol-4-yl)-1-{{[(1-phenyl-cyclobutylmethyl)-carbamoyl]-methyl}-[4-(pyridin-2-ylmethoxy)-benzyl]-carbamoyl}-ethyl-carbamic Acid benzyl Ester Step 1: [(4-(Pyridin-2-ylmethoxy)-benzyl)-amino]-acetic Acid methyl Ester According to Example 1, Step 1, by substituting 4-(2-pyridinylmethoxy)benzaldehyde (J. Het. Chem., 1988;25:129) for 4-benzyloxybenzaldehyde, the title compound was obtained as an oil (36.3% yield).
MS-CI: Calculated for M+1: 287; Found: 287.

Step 2: (S)-{(4-(Pyridin-2-ylmethoxy))-benzyl)-[2-benzyloxycarbonylamino-3-(1-trityl-1H-imidazol-4-yl)-propionyl]-amino}-acetic Acid methyl Ester According to Example 1, Step 2, by substituting the compound from Step 1 above for [( 4-benzyloxy-benzyl)-amino]-acetic acid methyl ester, the title compound was obtained as a white foam (90.1% yield).
MS-APCI: Calculated for M+1: 800.3; Found: 800.3.

Step 3: (S)-{(4-(Pyridin-2-ylmethoxy)-benzyl)-[2-benzyloxycarbonylamino-3-(1-trityl-1H-imidazol-4-yl)-propionyl]-amino}-acetic Acid According to Example 1, Step 3, by substituting the methyl ester from Step 2 above for (S)-{(4-benzyloxy-benzyl)-[2-benzyloxycarbonylamino-3-(1-trityl-1H-imidazol-4-yl)-propionyl]-amino}-acetic acid methyl ester, the title compound was obtained as a white foam (87.5% yield).
MS-APCI: Calculated for M+1: 786.3; Found: 786.3.

Step 4: (S)-[1-(((4-Pyridin-2-ylmethoxy)-benzyl)-{[(1-phenyl-cyclobutlymethyl)-carbamoyl]-methyl}-carbamonyl)-2-(1-trityl-1H-imidazol-4-yl )-ethyl]-carbamic Acid benzl Ester According to Example 1, Step 4, by substituting the acid from Step 3 above for (S)-{(4-benzyloxy-benzyl)-[2-benzyloxycarbonylamino-3-(1-trityl-1H-imidazol-4-yl)-propionyl]-amino}-acetic acid, the title compound was obtained as a clear oil (100% yield).
MS-APCI: Calculated for M+1: 929.4; Found: 929.2.

Step 5: (S)-(2-(1H-Imidazol-4-yl)-1-{{[1-phenyl-cyclobutylmethyl)-carbamoyl]-methyl}-[4-(pyridin-2-ylmethoxy)-benzyl]-carbamoyl}-ethyl)-carbamic Acid benzyl Ester According to Example 1, Step 5, by substituting the compound from Step 4 above for (S)-[1-((4-benzyloxy-benzyl)-{[(1-phenyl-cyclobutylmethyl)-carbamoyl]-methyl}-carbamoyl)-2-(1-trityl- 1H-imidazol-4-yl)-ethyl]-carbamic acid benzyl ester, the title compound was obtained as a white foam (87% yield).

Analysis calculated for $C_{40}H_{42}N_6O_5 \cdot 0.25DCM$: C, 68.28; H, 6.05; N, 11.87. Found: C, 68.23; H, 6.05; N, 11.90.
MS-APCI: Calculated for M+1: 687.3; Found: 687.2.

EXAMPLE 4

(S)-[1-((4-Methyl-benzyl)-{[(1-phenyl-cyclobutyl-methyl)-carbamoyl]-methyl}-carbamoyl)-2-(1H-imidazol-4-yl)-ethyl]-carbamic Acid Benzyl Ester Step 1: [(4-Methyl-benzyl)-amino]-acetic Acid methyl Ester According to Example 1, Step 1, by substituting 4-methylbenzaldehyde for 4-benzyloxybenzaldehyde, the title compound was obtained as a colorless oil (53% yield).
MS-CI: Calculated for M+1: 194; Found: 194.

Step 2: (S)-{(Methyl-benzyl)-[2-benzyloxy-carbonyamino-3-(1-trityl-1-imidazol-4-yl-propionl]-amino}-acetic Acid methyl Ester According to Example 1, Step 2, by substituting the compound from Step 1 above for [(4-benzyloxy-benzyl)-amino]-acetic acid methyl ester, the title compound was obtained as a white foam (71% yield).
MS-APCI: Calculated for M+1: 707.3; Found: 706.3.

Step 3: (S)-{(4-Methy-benzyl)-2-benzyloxy-carbonylamino-3-(1-trityl-1H-imidazol-4-yl)-propionyl]-amino}-acetic Acid According to Example 1, Step 3, by substituting the compound from Step 2 above for (S)-{(4-benzyloxy-benzyl)-[2-benzyloxycarbonylamino-3-(1-trityl-1H-imidazol-4-yl)-propionyl]-amino}-acetic acid methyl ester, the title compound was obtained as a white foam (100% yield).
MS-APCI: Calculated for M+1: 693.3; Found: 693.2.

Step 4: (S)-[1-((4-Methyl-benzyl)-{[(1-phenyl-cyclobutymethyl)-carbamoyl]-methyl}-carbamoyl)-2-(1-trityl-1H-imidazol-4-yl)-ethyl]-carbamic Acid benzyl Ester According to Example 1, Step 4, by substituting the compound from Step 3 above for (S)-{(4-benzyloxy-benzyl)-[2-benzyloxycarbonylamino-3-(1-trityl-1H-imidazol-4-yl)-propionyl]-amino}-acetic acid, the title compound was obtained as a white foam (67% yield).
MS-APCI: Calculated for M+1: 836.4; Found: 836.1.
Step 5: (S)-[1-((4-Methyl-benzyl)-{[(1-phenyl-cyclobutylmethyl)-carbamoyl]-methyl}-carbamoyl)-2-(1H-imidazol-4-yl)-ethyl]-carbamlc Acid Benzyl Ester According to Example 1, Step 5, by substituting the compound from Step 4 above for (S)-[1-((4-benzyloxy-benzyl)-{[(1-phenyl-cyclobutylmethyl)-carbamoyl]-methyl}-carbamoyl)-2-(1-trityl-1H-imidazol-4-yl)-ethyl]-carbamic acid benzyl ester, the title compound was obtained as a white foam (55% yield).
Analysis calculated for $C_{35}H_{39}N_5O_4 \cdot 0.13DCM$: C, 69.77; H, 6.54; N, 11.58. Found: C, 69.77; H, 6.38; N, 11.52
MS-APCI: Calculated for M+1: 594.3; Found: 594.2.

EXAMPLE 5

(S)-[1-((4-Benzyloxy-benzyl)-{[(1-phenyl-cyclopentylmethyl)-carbamoyl]-methyl}-carbamoyl)-2-(1H-imidazol-4-yl)-ethyl]-carbamic Acid benzyl Ester According to Example 1, Steps 4 and 5, by substituting C-(1-phenyl-cyclopentyl)-methylamine hydrochloride (U.S. Pat. No. 4,755,594; 1988) for C-(1-phenyl-cyclobutyl)-methylamine hydrochloride, 0.28 g (62% yield over 2 steps) of the title compound was obtained as a white foam.
Analysis calculated for $C_{42}H_{45}N_5O_5 \cdot 0.5 H_2O$: C, 71.17; H, 6.54; N, 9.88. Found: C, 71.44; H, 6.43; N, 9.93.
MS-APCI: Calculated for M+1: 700.3; Found: 700.3.

EXAMPLE 6

(S)-[1-((4-Methoxy-benzyl)-{[(1-phenyl-cyclobutyl-methyl)-carbamoyl]-methyl}-carbamoyl)-2-(1H-imidazol-4-yl)-ethyl]-carbamic Acid benzyl Ester was synthesized by a variation of Scheme 1 wherein the trityl protecting group was removed prior to formation of the C-terminal amide.
Step 1: [(4-Methoxy-benzyl)-amino]-acetic Acid Tert-butyl Ester According to Example 1, Step 1, by substituting 4-methoxybenzaldehyde for 4-benzyloxybenzaldehyde and glycine tert-butyl ester hydrochloride for glycine methyl ester hydrochloride, the title compound was obtained as a yellow oil (80% yield).
Step 2: (S)-{(4-Methoxy-benzyl)-[2-benzyloxy-carbonylamino-3-(1-trityl-1-H-imidazol-4-yl -propionyl]-amino}-acetic Acid Tert-butyl Ester According to Example 1, Step 2, by substituting the compound from Step 1 above for [(4-benzyloxy-benzyl)-amino]-acetic acid methyl ester, the title compound was obtained as a white foam (73% yield).
Step 3: (S)-{(4-Methoxy-benzyl)-[2-benzyloxycarbonyl-amino-3-(1H-imidazol-4-yl)-propionyl]-amino}-acetic Acid To a solution of the trityl compound from Step 2 above (3.93 g, 5.14 mmol) in DCM (25 mL) was added TFA (25 mL). The solution was stirred at room temperature for 3 hours and then concentrated. The residue was added to ether (300 mL) and cooled. The white tarry solid was collected by filtration to give 2.37 g (99% yield) of the title compound.
Step 4: (S)-[1-((4-Methoxy-benzyl)-{[(1-pheny-cyclobutylmethyl)-carbamoyl]-methyl}-carbamoyl)-2-(1H-imidazol-4-yl)-ethyl]-carbamic Acid benzyl Ester According to Example 1, Step 4, by substituting the compound from Step 3 above for (S)-{(4-benzyloxy-benzyl)-[2-benzyloxycarbonylamino-3-(1-trityl-1H-imidazol-4-yl)-propionyl]-amino}-acetic acid, the title compound was obtained as a white foam (17% yield). Final purification was accomplished by preparative C18 reverse phase high pressure liquid chromatography using a gradient of 0.1% TFA/acetonitrile in 0.1% TFA/$H_2O$.
Analysis calculated for $C_{35}H_{39}N_5O_5 \cdot 1.13$ TFA.0.4 $H_2O$: C, 59.99; H, 5.53; N, 9.39. Found: C, 59.99; H, 5.53; N, 9.26.
MS-APCI: Calculated for M+1: 610.3; Found: 610.3.

EXAMPLE 7

(S)-2-(3-Benzyl-3-methyl-ureido)-3-(1H-imidazol-4-yl)-N-(4 methyl-benyl)-N-{[(1-phenyl-cyclobutylmethy)-carbomyl]-methyl}-propionamide The title compound can be prepared according to Example 1, Step 1, substituting 4-methylbenzaldehyde for 4-benzyloxybenzaldehyde; Step 2, by substituting N-methyl-N-benzyl-urea-histidine (trityl) (Steps 1 and 2, below) for Cbz-His-(Trt); Step 3, using 1N NaOH in methanol/THF for LiOH:$H_2O$ in THF; Step 4, using DCC/HOBt as coupling reagents for BOP; and Step 5, using 80% aqueous acetic acid for 50% TFA in DCM. The title compound is obtained as a white foam; 0.16 g (57% yield).
Analysis calculated for $C_{36}H_{42}N_6O_3$: 0.16 $CH_2Cl_2$: C, 70.01; H, 6.88; N, 13.55. Found: C, 70.04; H, 6.86; N, 13.62.
MS-APCI: Calculated for M+1: 607.8; Found: 607.2.
Step 1: N-methyl-benzyl-urea-histidine-(trityl) methyl Ester Histidine-(trityl) methyl ester hydrochloride (2.0 g, 4.2 mmol) was suspended in DCM (20 mL), and the solution was washed twice with saturated $NaHCO_3$, and brine, dried over $MgSO_4$, and cooled to 0° C. Triethylamine (0.65 mL, 8.8 mmol) and 4-nitrophenyl chloroformate (0.93 g, 4.7 mmol) was added. The reaction was stirred at 0° C. under nitrogen for 1.5 hours. N-benzyl-N-methylamine (1.14 mL, 8.8 mmol) in DCM (10 mL) was then added slowly, and the reaction was stirred at room temperature overnight, under nitrogen. The solvent was removed, and ethyl acetate was added to the residue. The organic solution was washed twice with water, saturated $NaHCO_3$, brine, and dried over $MgSO_4$, and concentrated. Chromatography using 1:1 ethyl acetate:hexanes gave a foam; 1.19 g (50% yield).
Step 2: N-methyl-N-benzyl-urea-histidine-(trityl)

The methyl ester from Step 1 (1.19 g, 2.1 mmol) was dissolved in THF:methanol (10 mL of each). NaOH (1N) (6.3 mL, 6.3 mmol) was added, and the reaction was stirred overnight. The solvent was removed. HCl (1N) (6.3 mL) was added, and the product was extracted with ethyl acetate. The organic solution was then washed twice with brine, dried over $MgSO_4$, and concentrated to give a white foam; 1.4 g (100% yield).

EXAMPLE 8

(S)-2-(3-Benzyl-3-methyl-ureido)-N-(4-benzyloxy-benzyl)-3-(1H-imidazol-4-yl)-N-{[(1-phenyl-cyclobutylmethyl)-carbamoyl]-methyl}-propionamide The title compound can be prepared according to Example 1, Step 2, by substituting N-methyl-N-benzyl-urea-histidine (trityl) (Steps 1 and 2, Example 7) for Cbz-His-(Trt); Step 3, using 1N NaOH in methanol/THF for LiOH:$H_2O$ in THF; Step 4, using DCC/HOBt as coupling reagents for BOP; and Step 5, using 80% aqueous acetic acid for 50% TFA in DCM. The title compound is obtained as a white foam; 0.12 g (52% yield). Analysis calculated for $C_{42}H_{46}N_6O_4$: 0.33 $CH_2Cl_2$ C, 68.87; H, 6.33; N, 11.39. Found: C, 68.87; H, 6.43; N, 11.11.
MS-APCI: Calculated for M+1: 699.9; Found: 699.4.

EXAMPLE 9

(S)-[1-[(4-Benzyloxy-benyl)-({[1-(2,6-dichlorophenyl)-cyclobutylmethyl]-carbamoyl}-methyl)-carbamoyl]-2-(1H-imidazol-4-yl)-ethyl]-carbamic Acid benzyl Ester The title compound can be prepared according to Example 1, Step 3, using 1N NaOH in methanol/THF for LiOH:$H_2O$ in THF; Step 4, substituting [1-(2,6-dichlorophenyl)cyclobutyl] methylamine hydrochloride (Step 1, below) for C-(1-phenyl-cyclobutyl)methylamine hydrochloride. The title compound was purified by reversed-phase high pressure liquid chromatography (eluent: 0.1% aqueous TFA, and 0.1% TFA in acetonitrile) to give a white foam; 0.015 g (5% yield).

Analysis calculated for $C_{41}H_{39}N_5O_5Cl_2$: 1.68 $C_2H_1O_2F_3$: 1.01 $H_2O$: C, 55.36; H, 4.47; N, 7.28. Found: C, 55.36; H, 4.47; N, 7.26.
MS-APCI: Calculated for M+1: 752.2; Found: 752.6.

Step 1: [1-(2,6-dichlorophenyl) cyclobutyl]methylamine hydrochloride 1-(2,6-dichlorophenyl)-1-cyclobutanecarbonitrile (1 g, 4.4 mmol) was reduced with Raney nickel, in methanol/$NH_3$. The catalyst was removed and washed with methanol. The filtrate was concentrated, and diethyl ether (100 mL) was added to the residue. Concentrated HCl was added dropwise to precipitate the desired product; 1.05 g (100% yield).

EXAMPLE 10

[(S)-trans]-[1-(But-2-enyl-{[(1-phenyl-cyclobutylmethyl)-carbamoyl]-methyl}-carbamoyl)-2-(3H-imidazol-4-yl)-ethyl]-carbamic Acid benzyl Ester Step 1: Methyl 2-[(E)-2-butenylamino]acetate A suspension of (E)-2-buten-1-amine.HCl (5.37 g, 49.9 mmol) (Chem. Ber., 1984;117:1250) in acetonitrile (100 mL) was treated with methyl bromoacetate (4.72 mL, 49.9 mmol) and $Et_3N$ (14.0 mL, 99.8 mmol) and stirred at room temperature for 1 hour. The suspension was then heated at reflux overnight. Solution occurred at reflux temperature. After cooling, the precipitated $Et_3$NHCl was filtered off and the solvent removed under reduced pressure leaving 5.0 g of the crude product. Chromatography on silica gel, eluting with $CHCl_3$/MeOH (98:2) gave 1.41 g (19.8% yield) of the pure product as an oil.

Step 2: Methyl 2-[2-[(benzyloxy)carbonyl]amino-3-(1-trityl-1H-5-imidazolyl)propanoyl][(E)-2-butenyl]aminoacetate A solution of methyl 2-[(E)-2-butenylamino]acetate (from Step 1) (0.6 g, 4.2 mmol) in $CH_2Cl_2$ (50 mL) was cooled in ice and treated with of Z-His(Trt) (2.23 g, 4.2 mmol), diisopropylethylamine (2.2 mL, 12.6 mmol), and PyBOP (2.2 g, 4.2 mmol). After stirring at 0° for 15 minutes, the solution was allowed to stir at room temperature for 4 days. After removal of the solvent under reduced pressure, the residue was taken up in EtOAc, washed three times with $H_2O$, then with saturated NaCl. Drying over $MgSO_4$ and removal of the solvent under reduced pressure left 4.36 g of the crude product. Chromatography on silica gel, eluting with $CHCl_3$/MeOH (98:2) gave 2.23 g (81.1% yield) of the pure product as a white solid foam.
MS, m/z 657 (M+H$^+$).

Step 3: 2-[2-[(Benzyloxy)carbonyl]amino-3-(1-trityl-1H-5-imidazoyl)propanoyl][(E)-2-butenyl]aminoactic Acid A solution of the ester (from Step 2) (2.23 g, 3.4 mmol) in MeOH/dioxane (20 mL and 15 mL, respectively) was treated with 2N NaOH (7.0 mL, 14.0 mmol) and stirred at room temperature for 0.5 hours. After adding 2N HCl (7.0 mL, 14.0 mmol), the mixture was stripped to a solid. This was mixed with EtOAc/THF and filtered to remove NaCl. Removal of the solvent under reduced pressured left 2.06 g (94.5% yield) of the product as a white solid foam.
MS, m/z 643 (M+H$^+$).

Step 4: Benzyl N-2-[(E)-2-butenyl(2-oxo-2-[(1-phenycyclobutyl)methyl]aminoethyl)amino]-2-oxo-1-[(1-trityl-1H-4-imidazolyl)methyl]ethylcarbamate The compound (1 g, 1.6 mmol) from Step 3, was dissolved in methylene chloride (50 mL). HOBt (0.29 g, 2.1 mmol) was added followed by 0.5 M DCC/DCM (3.8 mL, 1.9 mmol), C-(1-phenyl-cyclobutyl)-methylamine hydrochloride (0.37 g, 1.9 mmol) and DIEA (0.61 mL, 3.5 mmol). The reaction was stirred at room temperature, under a nitrogen atmosphere for 2 days. The solution was filtered, the filtrate was concentrated under reduced pressure. The residue was taken up in ethyl acetate, and the organic solution was washed twice with 2N HCl, 1N NaHCO$_3$, and brine, dried over MgSO$_4$, filtered, and concentrated. Chromatography on silica gel, eluting with CHCl$_3$/CH$_3$OH (95:5) gave 0.97 g (77% yield) of the pure product.

Step 5: [(S)-trans]-[1-(But-2-enyl-{[(1-phenyl-cyclobutylmethyl)-carbamoyl]-methyl}-carbamoyl)-2-(3H-imidazol-4-yl)-ethyl]-carbamic Acid benzyl Ester The title compound was obtained by treating the compound from Step 4 (0.97 g, 1.2 mmol) with glacial acetic acid (20 mL) and water (5 mL) at reflux for 40 minutes. The reaction mixture was cooled, and concentrated under reduced pressure. The residue was taken up in ethyl acetate, and the organic solution was washed four times with saturated NaHCO$_3$, twice with brine, dried over MgSO$_4$, filtered, and concentrated. Chromatography on silica gel, eluting with CHCl$_3$/CH$_3$OH (0–6% CH$_3$OH in CHCl$_3$) gave 0.43 g (66% yield) of the pure product.

Analysis calculated for C$_{31}$H$_{37}$N$_5$O$_4$: 0.25 CHCl$_3$: C, 65.45; H, 6.55; N, 12.21. Found: C, 65.59; H, 6.61; N, 12.20.
MS-APCI: Calculated for M+1: 544.7; Found: 544.3.

EXAMPLE 11

(S)-[2-(3H-Imidazol-4-yl)-1-({[(1-phenyl-cyclobutylmethyl)-carbamoyl]-methyl}-propyl-carbamoyl-ethyl]-carbamic Acid benzyl Ester The title compound can be prepared according to Example 10, carrying out Step 1 as shown below. The title compound is obtained as a white foam; 0.25 g (66% yield).

Analysis calculated for C$_{30}$H$_{37}$N$_5$O$_4$.0.10 CHCl$_3$: C, 66.51; H, 6.88; N, 12.88. Found: C, 66.52; H, 6.84; N, 13.11.
MS-APCI: Calculated for M+1: 532.7; Found: 532.2.

Step 1: Methyl 2-(propylamino)acetate

A suspension of glycine methyl ester HCl (5.0 g, 39.8 mmol) in acetonitrile (100 mL) was treated with propyl bromide (3.7 mL, 39.8 mmol), and diisopropylethylamine (13.9 mL, 79.6 mmol). After stirring at room temperature for 1 hour, the mixture was heated at reflux overnight. Solution occurred at reflux temperature. The solvent was removed under reduced pressure and the residue triturated with Et$_2$O/EtOAc. Filtering and removal of the solvent under pressure left 1.13 g of the crude product. Chromatography on silica gel, eluting with CHCl$_3$/MeOH (98:2) gave 0.53 g (10.2% yield) of the product as a yellow oil.
MS, m/z 132 (M+H$^+$).

EXAMPLE 12

N-((1S)-1-(1H-4-imidazolylmethyl)-2-oxo-2-(2-oxo-2-[(1-phenylcyclobutyl)methyl]aminoethyl)[(1R)-1-phenylethyl]aminoethyl)carbamate The title compound can be prepared according to Example 10, Step 1, substituting R-α-methylbenzylamine for (E)-2-buten-1-amine.HCl; Step 2, using HATU for PyBOP; Step 3, using LiOH:H$_2$O in THF for 2N NaOH in methanol/dioxane. The title compound is obtained as a white foam; 0.51 g (66% yield).

Analysis calculated for C$_{35}$H$_{39}$N$_5$O$_4$.0.35 CH$_2$Cl$_2$: C, 68.10; H, 6.42; N,11.23. Found: C, 68.25; H, 6.46; N, 11.23. MS-APCI: Calculated for M+1: 594.7; Found: 594.2.

EXAMPLE 13

(S)-[1-((1,1-Dimethyl-2-phenyl-ethyl)-{[(1-phenyl-cyclobutylmethyl)-carbamoyl]-methyl}-carbamoyl)-2-(3H-imidazol-4-yl)-ethyl]-carbamic Acid benzyl Ester The title compound can be prepared according to Example 10, Step 1, substituting β,β-dimethylphenethylamine hydrochloride (Step A, below) for (E)-2-buten-1-amine.HCl; Step 2, using HATU and HOAt for PyBOP; Step 4, using PyBOP for DCC/HOBt; Step 5, using 95% TFA in DCM for glacial acetic acid in water. The title compound is obtained as a white foam; 0.121 g (12% yield).

Analysis calculated for C$_{37}$H$_{42}$N$_5$O$_4$.0.33 CH$_2$Cl$_2$: C, 69.11; H, 6.63; N, 10.79. Found: C, 69.10; H, 6.91; N, 11.00. MS-APCI: Calculated for M+1: 621.8; Foud: 622.2.

Step A: β,β-Dimethylphenethylamine for Hydrochloride

Sodium hydride (60% in oil) 17 g, 0.43 mol) was suspended in THF (150 mL) and cooled to 0° C. under nitrogen. Benzyl cyanide (22.2 g, 0.19 mol) in THF (30 mL) was added dropwise, and the reaction was left to stir for 1 hour. Iodomethane (24.9 mL, 0.4 mol) in THF (20 mL) was added dropwise at 0° C. The reaction was stirred at room temperature overnight, under nitrogen. The solution was filtered and the filtrate removed in vacuo. The residue was taken up in ethyl acetate (100 mL) and washed 3 times with 10% NaHSO$_3$, saturated NaHCO$_3$, brine, and dried over MgSO$_4$, concentrated; 22.74 g (92% yield).

Reduction of the above product was carried out in the presence of Raney nickel, in methanol/NH$_3$. The catalyst was removed and washed with methanol. The filtrate was concentrated, and diethyl ether (100 mL) was added to the residue. Concentrated HCl was added dropwise to precipitate the desired product; 24.8 g (86% yield).

PFT Inhibitory Activity

The protein:farnesyltransferase (PFT) or farnesyl protein transferase (FPT) inhibitory activity of compounds of the present invention were assayed in HEPES buffer (pH 7.4) containing 5 mM potassium phosphate and 20 μM ZnCl$_2$. The solution also contained 5 mM DTT (dithiothreitol), 5 mM MgCl$_2$ and 0.1% PEG 8000. Assays were performed in 96 well plates (Wallec) and employed solutions composed of varying concentrations of a compound of the present invention in 100% DMSO (dimethylsulfoxide). Upon addition of both substrates, radiolabeled farnesyl pyrophosphate ([1-$^3$H], specific activity 15–30 Ci/mmol, final concentration 134 nM) and (biotinyl)-Ahe-Thr-Lys-Cys-Val-Ile-Met ([3aS [3a alpha, 4 beta, 6a alpha]-hexahydro-2-oxo-1H-thieno[3,4-d]imidazole-5-pentanoic acid]-[7-aminoheptanoic acid]-Thr-Lys-Cys-Val-Ile-Met) (Ahe is 7-aminoheptanoic acid, Thr is threonine, Lys is lysine, Cys is cysteine, Val is valine, Ile is isoleucine and Met is methionine) (final concentration 0.2 μM), the enzyme reaction was started by addition of SF9 affinity purified rat farnesyl protein transferase. After incubation at 30° C. for 30 minutes, the reaction was terminated by diluting the reaction 2.5-fold with a stop buffer containing 1.5 M magnesium acetate, 0.2 M H$_3$PO$_4$, 0.5% BSA (bovine serum albumin), and strepavidin beads (Amersham) at a concentration of 1.3 mg/mL. After allowing the plate to settle for 30 minutes at room temperature, radioactivity was quantitated on a microBeta counter (Model 1450, Wallec). The assay was also carried out without 5 mM potassium phosphate.

Gel Shift Assay

Twenty-four hours after planting 2×10$^6$ ras-transformed cells per treatment condition, the farnesylation inhibitor is added at varying concentrations. Following an 18-hour incubation period, cells are lysed in phosphate-buffered saline containing 1% Triton X-100, 0.5% sodium deoxycholate, and 0.1% SDS (sodium dodecyl sulfate), pH 7.4 in the presence of several protease inhibitors (PMSF (phenylmethylsulfonylfluoride), antipain, leupeptin, pepstatin A, and aprotinin all at 1 μg/mL). Ras protein is immunoprecipitated from the supernatants by the addition of 3 μg v-H-ras Ab-2 (Y13-259 antibody from Oncogene Science). After overnight immunoprecipitation, 30 μL of a 50% protein G-Sepharose slurry (Pharmacia) is added followed by 45-minute incubation. Pellets are resuspended in 2× tris-glycine loading buffer (Novex) containing 5% β-mercaptoethanol and then denatured by 5 minutes boiling prior to electrophoresis on 14% Tris-glycine SDS gels. Using Western transfer techniques, proteins are transferred to nitrocellulose membranes followed by blocking in blocking buffer. Upon overnight incubation with primary antibody (pan-ras Ab-2 from Oncogene Science), an antimouse HRP (horse radish peroxidase) conjugate secondary antibody (Amersham) is employed for detection of the ras protein. Blots are developed using ECL(enhanced chemiluminescence) techniques (Amersham).

Clonogenic Assay (6 well plates)

Sometime previous to setting up an actual test:
1. Make up 1.5% Bacto Agar in Milli-Q water and autoclave.
2. Make up 500 mL 2× DMEM-HG without phenol red by combining the following:
   1 bottle DMEM base powder (Sigma D-5030)
   4.5 g glucose
   3.7 g sodium bicarbonate
   0.11 g sodium pyruvate
   20 mL of 200 mM L-glutamine (Sigma G-7513)
   1 mL pen-strep (GibcoBRL No. 15140-023)
   Adjust pH to 7.1 with HCl; filter sterilize.
1. Set up makeshift water bath (beaker of water with thermometer, on hot plate) in the hood. Keep water temperature between 37° C. to 43° C.
2. Autoclave 1.5% Bacto Agar for approximately 2 minutes on high, or until completely melted. Then let it cool somewhat before using it. (You can keep it from resolidifying by setting the bottle on the hot plate.)

| Bottom Layer (0.6% agar) | Top Layer (0.3% agar) |
|---|---|
| 20% calf serum | 20% calf serum |
| 40% 2X DMEM | 50% 2X DMEM |
| 40% Bacto Agar (1.5%) | 20% Bacto Agar (1.5%) |
|  | 10% sterile H$_2$O × μL |

-continued

| Bottom Layer (0.6% agar) | Top Layer (0.3% agar) |
|---|---|
| | cell suspension (to = 5000 cells/well) (H61 cells: NIH transformed 3T3 H-ras cells) |

Depending on the volume of each layer needed, use either 50 mL conical tubes or 200 mL turnip tubes which can be floated in the "water bath".

4. Add 1 mL of bottom layer agar/medium to each well: deliver 1 mL warm agar/medium to a well; then using the tip of the pipet, spread the agar/medium around to completely cover the bottom. Repeat with next well. Do not add the last mL in the pipet to a well, it leads to bubbles.
5. Allow the plates to set at room temperature for about 5 minutes until the bottom layer solidifies.
6. Label sterile Falcon 2054 (12×75 mm) tubes and add appropriate volume of drug solutions into them.
7. Aliquot 4 µL of DMSO or drug solution per 1 mL of agar/medium to appropriate tubes; then add the agar/medium/cells to each tube. Always add 1 mL more than will actually be needed. Mix up and down in the pipet (gently); then deliver 1 mL to the center of each well. The upper layer is less viscous, so it will generally spread out over the bottom layer unaided. If necessary, rotate the plane of the plate gently to spread the top layer evenly over the bottom layer.
8. Let plates set for 5 or 10 minutes at room temperature to solidify, then put into 5% $CO_2$, 37° C. incubator.
9. On Day 13, add 0.5 mL of INT (tetrazolium 1 mg/mL in Milli-Q $H_2O$, filter sterilized) and return plates to incubator.
10. Count colonies.

The data in the table below shows farnesyl protein transferase inhibitory activity, activity in the gel shift assay, and activity in the Clonogenic Assay of compounds of the present invention.

| | PFT Inhibitory Activity | | | |
|---|---|---|---|---|
| Example No. | $IC_{50}$ (µM) HEPES | $IC_{50}$ (µM) HEPES and 5 mM $K_3PO_4$ | Gel Shift (µM) M.E.D.* | Clonogenic Assay $IC_{50}$ (µM) |
| 1 | 0.075 | 0.006 | 0.02 | 0.047 |
| 2 | 0.15 | 0.006 | 0.02 | 0.18 |
| 3 | 0.14 | 0.0017 | 0.002 | 0.14 |
| 4 | 0.26 | 0.0054 | 0.01 | NT |
| 5 | 0.32 | 0.018 | 0.2 | 0.32 |
| 6 | 0.26 | 0.0029 | 0.002 | 0.21 |
| 7 | 0.014 | 0.003 | 0.01 | NT |
| 8 | 0.068 | 0.015 | 0.01 | NT |
| 9 | 7.0 | 0.18 | >0.2 | NT |
| 10 | <0.001 | 0.36 | ≦0.05 | NT |
| 11 | <0.001 | 0.33 | ≦0.05 | NT |
| 12 | 0.002 | 0.34 | ≦0.05 | NT |

*M.E.D. is minimal effective dose to observe inhibition of ras farnesylation
NT - Not tested.

In Vivo Activity

Female NCR-NU mice were randomized and then inoculated with trocar fragments of H61 xenografts obtained from donor animals on Day 0 of the experiment. H61 cells are NIH3T3 cells that have been transfected and transformed with mutant human H-ras. The animals were then re-randomized to treatment groups. Tumor-bearing mice were then treated via subcutaneous (SC) or interperitoneal (IP) injections of Example 1 every 12 hours at various dose levels for 14 days beginning on Day 1. Tumors were measured with calipers in two orthogonal dimensions several times per week for the duration of the experiment. Tumor burdens in milligrams were estimated from the caliper measurements by standard methods ($mg = axb^2/2$, where a and b are the measurements of the major and minor axes of the tumor, respectively.) Inhibition of tumor growth was assessed at the last day of treatment (14). Example 1 significantly inhibited tumor growth in this assay. When given SC at 96 mg/kg/injection, the median tumor burden of the treated group was 672 mg compared to a median burden of 2508 mg for the vehicle treated control group, representing a 73% inhibition of tumor growth. In mice given Example 1 IP at either 37 or 23 mg/kg/injection, no tumors were evident at the sites of inoculation, indicating complete (100%) inhibition of tumor growth.

What is claimed is:

1. A compound having the Formula I

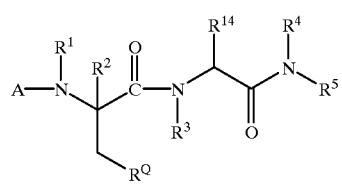

wherein $R^Q$ is

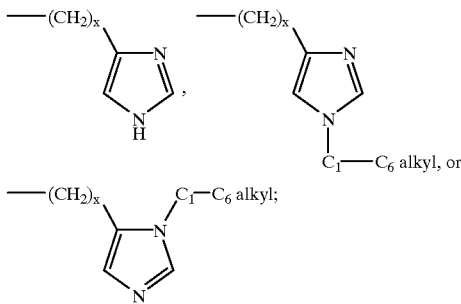

x is 0 or 1;

each $R^{14}$ is independently hydrogen or $C_1$–$C_6$ alkyl;

A is —$COR^a$, —$CO_2R^{a\prime}$, —$CONHR^{a\prime}$, —$CSR^a$,

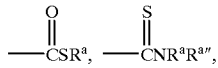

—$C(S)OR^{a\prime}$, —$C(S)NHR^{a\prime}$, —$SO_2R^a$, or —$CONR^aR^{a\prime\prime}$;

$R^a$, $R^{a\prime}$, and $R^{a\prime\prime}$ are independently $C_1$–$C_6$ alkyl, —$(CR^{14}R^{14})_m$-cycloalkyl, —$(CR^{14}R^{14})_m$-aryl, or —$(CR^{14}R^{14})_m$-heteroaryl;

each m is independently 0 to 3;

$R^1$, $R^2$, and $R^4$ are independently hydrogen or $C_1$–$C_6$ alkyl;

$R^3$ is

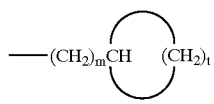

$C_1$–$C_6$ alkyl, $C_2$–$C_6$ alkenyl, —$(CR^{14}R^{14})_m$-naphthyl, —$(CH_2)_v CO_2 R^{14}$, —$(CH_2)_t NR^{14}R^{14}$, —$(CH_2)_v$—O—$C_1$–$C_6$ alkyl, —$(CH_2)_t$—OH, —$(CH_2)_t$-morpholino, —$(CH_2)_t$—N⌒N—$R^{14}$, —$(CH_2)_v$—⌬N—$R^{14}$, —$(CR^{14}R^{14})_m$-(phenyl substituted with $R^b$), or —$(CR^{14}R^{14})_m$-(heteroaryl substituted with $R^b$);

t is 2 to 6;
v is 1 to 6;
$R^b$ is —O-phenyl, —O-benzyl, halogen, $C_1$–$C_6$ alkyl, hydrogen, —$OC_1$–$C_6$ alkyl, —$NH_2$, —$NHR^a$, —$NR^a R^{a'}$, —$\overset{O}{\overset{\|}{C}}C_1$—$C_6$ alkyl, —$\overset{O}{\overset{\|}{C}}$-aryl, —OH, —$\overset{O}{\overset{\|}{C}}NH_2$, —$\overset{O}{\overset{\|}{C}}NHR^a$, —$\overset{O}{\overset{\|}{C}}NR^a R^{a'}$, —$NH\overset{O}{\overset{\|}{C}}R^a$, —$O(CH_2)_y NR^a R^{a'}$, —$CF_3$, —$NO_2$, —$\overset{O}{\overset{\|}{C}}OH$, —$\overset{O}{\overset{\|}{C}}OC_1$—$C_6$ alkyl, —CN, —$OPO_3H_2$, —$CH_2PO_3H_2$, —$\overset{O}{\overset{\|}{C}}O$ aryl, —$N_3$, —$OPO_3H_2$, —$CF_2CF_3$, —$SO_2R^a$, —$SO_2NR^a R^{a'}$, —CHO, —$OCOCH_3$, —$O(CH_2)_m$-aryl, —$O(CH_2)_m$-cycloalkyl, —$(CH_2)_m$-aryl, —$(CH_2)_m$-cycloalkyl, —$(CH_2)_m$-heteroaryl, or —CH=CHC$_6$H$_5$, or —$O(CH_2)_m$-heteroaryl;

y is 2 or 3;
$R^5$ is

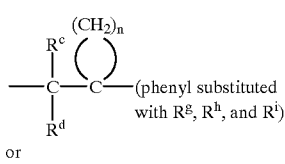

or

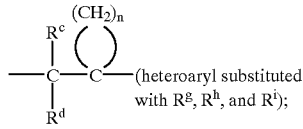

each n is independently 2, 3, or 4;

$R^i$, $R^g$, and $R^h$ are independently hydrogen, halogen, —$OC_1$–$C_6$ alkyl, $C_1$–$C_6$ alkyl, —CN, —$OPO_3H_2$, —$CH_2PO_3H_2$, —O-phenyl, —O-benzyl, —$\overset{O}{\overset{\|}{C}}NH_2$, —$\overset{O}{\overset{\|}{C}}NHR^a$, —$\overset{O}{\overset{\|}{C}}NR^a R^{a'}$, —$NH\overset{O}{\overset{\|}{C}}R^a$, —$O(CH_2)_y NR^a R^{a'}$, —$NH_2$, —$NHR^a$, —$NR^a R^{a'}$, —$\overset{O}{\overset{\|}{C}}C_1$—$C_6$ alkyl, —$\overset{O}{\overset{\|}{C}}$-aryl, —OH, —$CF_3$, —$NO_2$, —$\overset{O}{\overset{\|}{C}}OH$, —$\overset{O}{\overset{\|}{C}}OC_1$—$C_6$ alkyl, —$\overset{O}{\overset{\|}{C}}O$ aryl, —$N_3$, —$CF_2CF_3$, —$SO_2R^a$, —$SO_2NR^a R^{a'}$, —CHO, or —$OCOCH_3$; and $R^c$ and $R^d$ are independently $C_1$–$C_6$ alkyl, —$(CH_2)_m$-cycloalkyl or hydrogen, and the pharmaceutically acceptable salts, esters, amides, and prodrugs thereof.

2. A compound in accordance with claim 1 wherein $R^1$ is hydrogen, $R^2$ is hydrogen, $R^4$ is hydrogen, $R^{14}$ is hydrogen or methyl; and A is

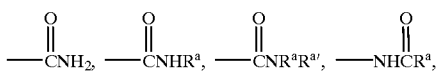

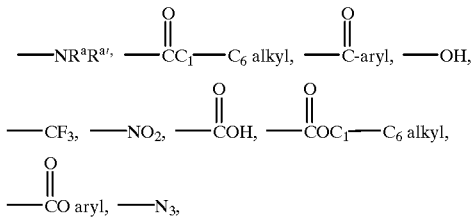

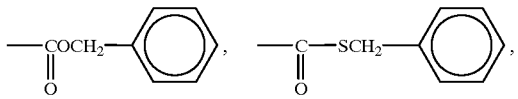

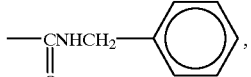

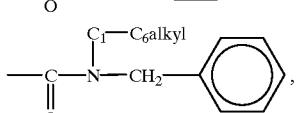

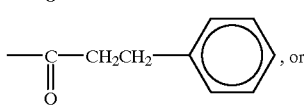

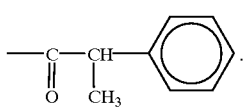

3. A compound in accordance with claim 1 wherein $R^3$ is

—$(CH_2)_m CH$⌒$(CH_2)_t$ $C_1$–$C_6$ alkyl, $C_2$–$C_6$ alkenyl, —$(CH_2)_m$-(phenyl substituted with $R^b$) or —$(CH_2)_m$-(heteroaryl substituted with $R^b$);

$R^1$ is hydrogen, $R^2$ is hydrogen, $R^4$ is hydrogen, and $R^{14}$ is hydrogen or methyl.

4. A compound according to claim 1 wherein $R^5$ is

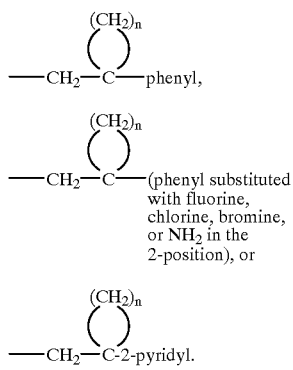

5. A compound having the Formula II

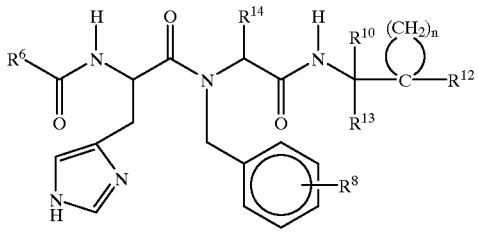

wherein $R^6$ is —O-benzyl,

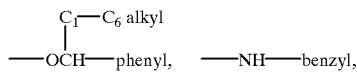

—N($C_1$–$C_6$ alkyl)-benzyl, or —$SCH_2$-phenyl;

$R^8$ is hydrogen, halogen, $C_1$–$C_6$ alkyl, —O-benzyl, —$OCH_2$-pyridyl, —$OC_1$–$C_6$ alkyl, —$CF_3$, —OH, or -phenyl;

$R^{10}$ and $R^{13}$ are independently hydrogen or $C_1$–$C_6$ alkyl;

each n is independently 2, 3, or 4;

$R^{12}$ is

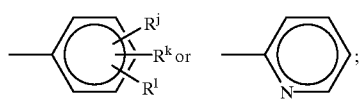

and $R^{14}$ is hydrogen or methyl;

$R^j$, $R^k$, and $R^l$ are independently hydrogen, —$NH_2$, —$NHR^a$, halogen, —$OC_1$–$C_6$ alkyl or $C_1$–$C_6$ alkyl, and the pharmaceutically acceptable salts, esters, amides and prodrugs thereof.

6. A compound having the Formula III

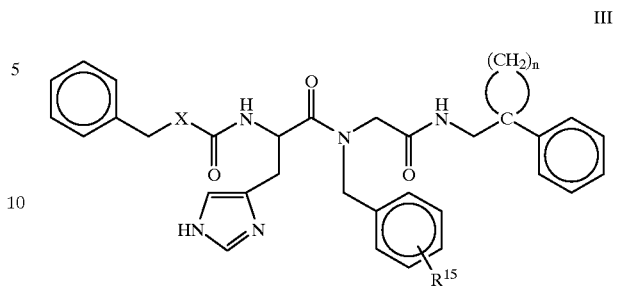

wherein
each n is 2, 3, or 4;
X is NH, O, or —$NCH_3$;
$R^{15}$ is —O-benzyl, —$CF_3$, hydrogen, halogen, —OH, -phenyl, —$C_1$–$C_6$ alkyl, —O-$CH_2$-pyridyl, or —$OC_1$–$C_6$ alkyl;
and the pharmaceutically acceptable salts, esters, amides, and prodrugs thereof.

7. A compound having the Formula IV

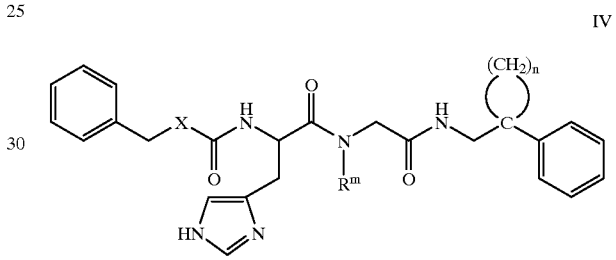

wherein
X is NH, O, or —$NCH_3$;
$R^{14}$ is hydrogen or $C_1$–$C_6$ alkyl;
$R^m$ is $C_1$–$C_6$ alkyl, $C_2$–$C_6$ alkenyl, —$(CH_2)_t NR^{14}R^{14}$, —$(CH_2)_v$—O—$C_1$–$C_6$ alkyl, —$(CH_2)_t$—OH, —$(CH_2)_t$-morpholino,

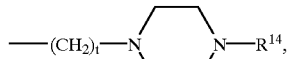

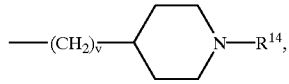

—$(CH_2)_v$—$CO_2R^{14}$, or —$(CH_2)_m CH$ $(CH_2)_t$;

n is 2, 3, or 4;
m is 0 to 3;
t is 2 to 6; and
v is 1 to 6.

8. A pharmaceutically acceptable composition that comprises a compound of claim 1.

9. A pharmaceutically acceptable composition that comprises a compound of claim 5.

10. A pharmaceutically acceptable composition that comprises a compound of claim 6.

11. A method of treating restenosis, the method comprising administering to a patient having restenosis or a risk of having restenosis a therapeutically effective amount of a compound of claim 1.

12. A method of treating restenosis, the method comprising administering to a patient having restenosis or a risk of having restenosis a therapeutically effective amount of a compound of claim 5.

13. A method of treating restenosis, the method comprising administering to a patient having restenosis or a risk of having restenosis a therapeutically effective amount of a compound of claim 6.

14. A method of treating cancer, the method comprising administering to a patient having cancer a therapeutically effective amount of a compound of claim 1.

15. A method of treating cancer, the method comprising administering to a patient having cancer a therapeutically effective amount of a compound of claim 5.

16. A method of treating cancer, the method comprising administering to a patient having cancer a therapeutically effective amount of a compound of claim 6.

17. The compounds:

(S)-[1-((4-Benzyloxy-benzyl)-{[(1-phenyl-cyclobutylmethyl)-carbamoyl]-methyl}-carbamoyl)-2-(1H-imidazol-4-yl)-ethyl]-carbamic acid benzyl ester;

(S)-[1-((4-Benzyloxy-benzyl)-{[(1-phenyl-cyclopropylmethyl)-carbamoyl]-methyl}-carbamoyl)-2-(1H-imidazol-4-yl)-ethyl]-carbamic acid benzyl ester;

(S)-[1-((4-Benzyloxy-benzyl)-{[(1-phenyl-cyclopentylmethyl)-carbamoyl]-methyl}-carbamoyl)-2-(1H-imidazol-4-yl)-ethyl]-carbamic acid benzyl ester;

(S)-[1-((4-Phenyl-benzyl)-{[(1-phenyl-cyclobutylmethyl)-carbamoyl]-methyl}-carbamoyl)-2-(1H-imidazol-4-yl)-ethyl]-carbamic acid benzyl ester;

(S)-[1-((4-Methoxy-benzyl)-{[(1-phenyl-cyclobutylmethyl)-carbamoyl]-methyl}-carbamoyl)-2-(1H-imidazol-4-yl)-ethyl]-carbamic acid benzyl ester;

(S)-[1-((4-Methyl-benzyl)-{[(1-phenyl-cyclobutylmethyl)-carbamoyl]-methyl}-carbamoyl)-2-(1H-imidazol-4-yl)-ethyl]-carbamic acid benzyl ester;

(S)-N-(4-Benzyloxy-benzyl)-2-(3-benzyl-ureido)-3-(1H-imidazol-4-yl)-N-{[(1-phenyl-cyclobutylmethyl)-carbamoyl]-methyl}-propionamide;

(S)-2-(3-Benzyl-3-methyl-ureido)-N-(4-benzyloxy-benzyl)-3-(1H-imidazol-4-yl)-N-{[(1-phenyl-cyclobutylmethyl)-carbamoyl]-methyl}-propionamide;

(S)-[1-((4-Benzyloxy-benzyl)-{[(1-phenyl-cyclobutylmethyl)-carbamoyl]-methyl}-carbamoyl)-2-(1H-imidazol-4-yl)-ethyl]-thiocarbamic acid S-benzyl ester;

(S)-(2-(1H-Imidazol-4-yl)-1-{{[(1-phenyl-cyclobutylmethyl)-carbamoyl]-methyl}-[4-(pyridin-2-ylmethoxy)-benzyl]-carbamoyl}-ethyl)-carbamic acid benzyl ester;

(S)-(1-((Cyclohexyl-methyl)-{[(1-phenyl-cyclobutylmethyl)-carbamoyl]-methyl}-carbamoyl)-2-(1H-imidazol-4-yl)-ethyl]-carbamic acid benzyl ester; and (S)-(1-((Isobutyl)-{[(1-phenyl-cyclobutylmethyl)-carbamoyl]-methyl}-carbamoyl)-2-(1H-imidazol-4-yl)-ethyl]-carbamic acid benzyl ester.

18. The compounds:

(S)-2-(3-Benzyl-3-methyl-ureido)-3-(1H-imidazol-4-yl)-N-(4-methyl-benzyl)-N-{[(1-phenyl-cyclobutylmethyl)-carbamoyl]-methyl}-propionamide;

(S)-[1-[(4-Benzyloxy-benzyl)-({[1-(2,6-dichloro-phenyl)-cyclobutylmethyl]-carbamoyl}-methyl)-carbamoyl]-2-(1H-imidazol-4-yl)-ethyl]-carbamic acid benzyl ester;

[(S)-trans]-[1-(But-2-enyl-{[(1-phenyl-cyclobutylmethyl)-carbamoyl]-methyl}-carbamoyl)-2-(3H-imidazol-4-yl)-ethyl]-carbamic acid benzyl ester;

(S)-[2-(3H-Imidazol-4-yl)-1-({[(1-phenyl-cyclobutylmethyl)-carbamoyl]-methyl}-propyl-carbamoyl)-ethyl]-carbamic acid benzyl ester;

Benzyl N-((1S)-1-(1H-4-imidazolylmethyl)-2-oxo-2-(2-oxo-2-[(1-phenylcyclobutyl)methyl]-aminoethyl)[(1S)-1-phenylethyl]aminoethyl)-carbamate; and (S)-[1-((1,1-Dimethyl-2-phenylethyl)-{[(1-phenyl-cyclobutylmethyl)-carbamoyl]-methyl}-carbamoyl)-2-(3H-imidazol-4-yl)-ethyl]-carbamic acid benzyl ester.

19. The compounds:

Benzyl N-[(1S)-2-[(2-hydroxyethyl)(2-oxo-2-[(1-phenylcyclobutyl)methyl]aminoethyl)amino]-1-(1H-4-imidazolylmethyl)-2-oxoethyl]carbamate;

3-[[(2S)-2-[(Benzyloxy)carbonyl]amino-3-(1H-4-imidazolyl)propanoyl](2-oxo-2-[(1-phenylcyclobutyl)methyl]aminoethyl)amino]propanoic acid;

Methyl 3-[[(2S)-2-[(benzyloxy)carbonyl]amino-3-(1H-4-imidazolyl)propanoyl](2-oxo-2-[(1-phenylcyclobutyl)methyl]aminoethyl)amino]propanoate;

Benzyl N-[(1S)-2-[(2-aminoethyl)(2-oxo-2-[(1-phenylcyclobutyl)methyl]aminoethyl)amino]-1-(1H-4-imidazolylmethyl)-2-oxoethyl]carbamate;

Benzyl N-(1S)-1-(1H-4-imidazolylmethyl)-2-[[2-(methylamino)ethyl](2-oxo-2-[(1-phenylcyclobutyl)methyl]aminoethyl)amino]-2-oxoethylcarbamate;

Benzyl N(1S)-1-(1H-4-imidazolylmethyl)-2-[(2-(methoxyethyl)(2-oxo-2-[(1-phenylcyclobutyl)methyl]aminoethyl)amino]-2-oxoethylcarbamate;

Benzyl N-(1S)-1-(1H-4-imidazolylmethyl)-2-[(2-(morpholinoethyl)(2-oxo-2-[(1-phenylcyclobutyl)methyl]aminoethyl)amino]-2-oxoethylcarbamate;

Benzyl N-(1S)-1-(1H-4-imidazolylmethyl)-2-[(2-(methyl-2-phenylpropyl)(2-oxo-2-[(1-phenylcyclobutyl)methyl]aminoethyl)amino]-2-oxoethylcarbamate; and 1-Phenylethyl N-[(1S)-2-[[4-(benzyloxy)-1,5-cyclohexadienyl]methyl(2-oxo-2-[(1-phenylcyclobutyl)methyl]aminoethyl)amino]-1-(1H-4-imidazolylmethyl)-2-oxoethyl]carbamate.

20. The method of claim 14 wherein the cancer is lung cancer, colon cancer, breast cancer, pancreatic cancer, thyroid cancer, or bladder cancer.

\* \* \* \* \*

UNITED STATES PATENT AND TRADEMARK OFFICE
CERTIFICATE OF CORRECTION

PATENT NO. : 6,281,194 B1
DATED : August 28, 2001
INVENTOR(S) : Annette M. Doherty et al.

It is certified that error appears in the above-identified patent and that said Letters Patent is hereby corrected as shown below:

<u>Column 30,</u>
Line 56, " "

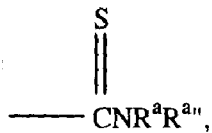

should read -- --

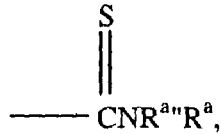

<u>Column 31,</u>
Line 45, delete "—OPO$_3$H$_2$,"

Signed and Sealed this

Eighth Day of April, 2003

JAMES E. ROGAN
*Director of the United States Patent and Trademark Office*